（12） United States Patent
Lin et al.

(10) Patent No.: US 8,618,144 B2
(45) Date of Patent: Dec. 31, 2013

(54) PYRROLIDINE-DERIVED BETA 3 ADRENERGIC RECEPTOR AGONISTS

(75) Inventors: Peter Lin, Edison, NJ (US); Lehua Chang, Ramsey, NJ (US); Scott D. Edmondson, Clark, NJ (US)

(73) Assignee: Merck Sharp & Dohme Corp, Rahway, NJ (US)

( * ) Notice: Subject to any disclaimer, the term of this patent is extended or adjusted under 35 U.S.C. 154(b) by 0 days.

(21) Appl. No.: 13/319,250

(22) PCT Filed: Apr. 28, 2010

(86) PCT No.: PCT/US2010/032733
§ 371 (c)(1),
(2), (4) Date: Nov. 7, 2011

(87) PCT Pub. No.: WO2010/129326
PCT Pub. Date: Nov. 11, 2010

(65) Prior Publication Data
US 2012/0053181 A1    Mar. 1, 2012

Related U.S. Application Data

(60) Provisional application No. 61/176,654, filed on May 8, 2009.

(51) Int. Cl.
*A01N 43/64*    (2006.01)
*A61K 31/41*    (2006.01)
*C07D 233/02*   (2006.01)

(52) U.S. Cl.
USPC ........ 514/359; 548/125; 548/255; 548/262.2; 548/300.1; 548/356.1; 548/59

(58) Field of Classification Search
USPC ................ 548/125, 255, 262.2, 300.1, 356.1; 514/359
See application file for complete search history.

(56) References Cited

U.S. PATENT DOCUMENTS

| 5,451,677 A | 9/1995 | Fisher et al. |
| 5,506,256 A | 4/1996 | Kobayashi et al. |
| 2002/0028835 A1 | 3/2002 | Hu et al. |

FOREIGN PATENT DOCUMENTS

| EP | 0 279 707 | 8/1988 |
| WO | WO02/06232 | 1/2002 |

OTHER PUBLICATIONS

Pallavicini, M. et al, 5-(2-Pyrrolidinyl)oxazolidinones and 2-(2-pyrrolidinyl)benzodioxanes: Synthesis of all the stereoisomers and α4β2 nicotinic affinity; Bioorganic & Medicinal Chemistry Letters, vol. 19, Issue 3, Feb. 1, 2009, pp. 854-859.
EP Supplementary Search Report for EP 10772559 Dated Sep. 6, 2012.
Prathipati et al., "Characterization of b3-adrenergic receptor: determination of pharmacophore and 3D QSAR model for b3 adrenergic receptor agonism", Journal of Computer Aided Molecular Design, vol. 19, p. 93-110 (2005).

*Primary Examiner* — Paul V. Ward
(74) *Attorney, Agent, or Firm* — Patricia A. Shatynski; Valerie J. Camara

(57) ABSTRACT

The present invention provides compounds of Formula (I), pharmaceutical compositions thereof, and method of using the same in the treatment or prevention of diseases mediated by the activation of β3-adrenoceptor.

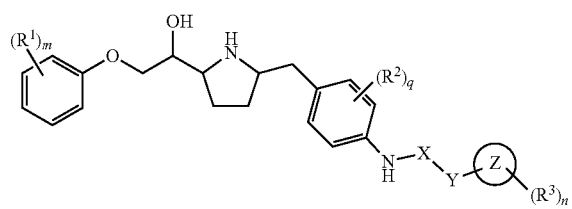

15 Claims, No Drawings

PYRROLIDINE-DERIVED BETA 3 ADRENERGIC RECEPTOR AGONISTS

CROSS REFERENCE TO RELATED APPLICATIONS

This application is a U.S. National Phase application under 35 U.S.C. §371 of PCT Application No. PCT/US2010/032733, filed Apr. 28, 2010, which claims priority under 35 U.S.C. §119(e) from U.S. Provisional Application Ser. No. 61/176,654, filed May 8, 2009.

BACKGROUND OF THE INVENTION

The function of the lower urinary tract is to store and periodically release urine. This requires the orchestration of storage and micturition reflexes which involve a variety of afferent and efferent neural pathways, leading to modulation of central and peripheral neuroeffector mechanisms, and resultant coordinated regulation of sympathetic and parasympathetic components of the autonomic nervous system as well as somatic motor pathways. These proximally regulate the contractile state of bladder (detrusor) and urethral smooth muscle, and urethral sphincter striated muscle.

β Adrenergic receptors (βAR) are present in detrusor smooth muscle of various species, including human, rat, guinea pig, rabbit, ferret, dog, cat, pig and non-human primate. However, pharmacological studies indicate there are marked species differences in the receptor subtypes mediating relaxation of the isolated detrusor; β1AR predominate in cats and guinea pig, β2AR predominate in rabbit, and β3AR contribute or predominate in dog, rat, ferret, pig, cynomolgus and human detrusor. Expression of βAR subtypes in the human and rat detrusor has been examined by a variety of techniques, and the presence of β3AR was confirmed using in situ hybridization and/or reverse transcription-polymerase chain reaction (RT-PCR). Real time quantitative PCR analyses of β1AR, β2AR and β3AR mRNAs in bladder tissue from patients undergoing radical cystectomy revealed a preponderance of β3AR mRNA (97%, cf 1.5% for β1AR mRNA and 1.4% for β2AR mRNA). Moreover, β3AR mRNA expression was equivalent in control and obstructed human bladders. These data suggest that bladder outlet obstruction does not result in downregulation of β3AR, or in alteration of β3AR-mediated detrusor relaxation. β3AR responsiveness also has been compared in bladder strips obtained during cystectomy or enterocystoplasty from patients judged to have normal bladder function, and from patients with detrusor hyporeflexia or hyperreflexia. No differences in the extent or potency of β3AR agonist mediated relaxation were observed, consistent with the concept that the β3AR activation is an effective way of relaxing the detrusor in normal and pathogenic states.

Functional evidence in support of an important role for the β3AR in urine storage emanates from studies in vivo. Following intravenous administration to rats, the rodent selective β3AR agonist CL316243 reduces bladder pressure and in cystomeric studies increases bladder capacity leading to prolongation of micturition interval without increasing residual urine volume.

Overactive bladder is characterized by the symptoms of urinary urgency, with or without urgency urinary incontinence, usually associated with frequency and nocturia. The prevalence of OAB in the United States and Europe has been estimated at 16 to 17% in both women and men over the age of 18 years. Overactive bladder is most often classified as idiopathic, but can also be secondary to neurological conditions, bladder outlet obstruction, and other causes. From a pathophysiologic perspective, the overactive bladder symptom complex, especially when associated with urge incontinence, is suggestive of detrusor overactivity. Urgency with or without incontinence has been shown to negatively impact both social and medical well-being, and represents a significant burden in terms of annual direct and indirect healthcare expenditures. Importantly, current medical therapy for urgency (with or without incontinence) is suboptimal, as many patients either do not demonstrate an adequate response to current treatments, and/or are unable to tolerate current treatments (for example, dry mouth associated with anticholinergic therapy).

Therefore, there is need for new, well-tolerated therapies that effectively treat urinary frequency, urgency and incontinence, either as monotherapy or in combination with available therapies. Agents that relax bladder smooth muscle, such as β3AR agonists, are expected to be effective for treating such urinary disorders.

SUMMARY OF THE INVENTION

The present invention relates to novel β3AR agonists, pharmaceutical compositions containing them, as well as methods for the treatment or prophylaxis of disorders mediated through the β3AR such as urinary incontinence using such novel compounds.

DESCRIPTION OF THE INVENTION

Described herein are compounds of structural Formula I, or pharmaceutically acceptable salts thereof:

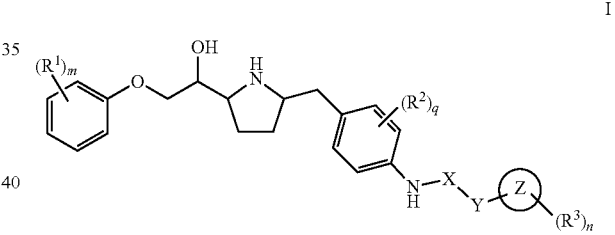

I wherein
m is 0, 1, 2, 3, or 4;
n is 0, 1, 2, 3, 4, or 5;
p is 0, 1, or 2;
q is 0, 1, 2, 3, or 4;
X is —CO— or —SO$_2$—;
Y is selected from the group consisting of:
  (1) C$_1$-C$_3$ alkylene, optionally substituted with —NR$^2$R$^2$ or hydroxy,
  (2) —N(R$^6$)—,
  (3) —O—,
  (4) a bond, and
  (5) phenylene, optionally substituted with 1 to 3 groups independently selected from R$^1$;
Z is selected from the group consisting of:
  (1) a bond,
  (2) phenyl,
  (3) naphthyl,
  (4) a 5- or 6-membered heterocyclic ring with from 1 to 4 heteroatoms selected from oxygen, sulfur and nitrogen,
  (5) a benzene ring fused to a C$_5$-C$_{10}$ carbocyclic ring,
  (6) a benzene ring fused to a 5- or 6-membered heterocyclic ring with from 1 to 4 heteroatoms selected from oxygen, sulfur and nitrogen, (7) a 5- or 6-membered heterocyclic ring with from 1 to 4 heteroatoms selected from oxygen, sulfur and nitrogen fused to a 5- or 6-membered heterocyclic ring with from 1 to 4 heteroatoms selected from oxygen, sulfur and nitrogen, and (8) a 5- or 6-membered heterocyclic ring with from 1 to 4 heteroatoms selected from oxygen, sulfur and nitrogen fused to a $C_5$-$C_{10}$ carbocyclic ring;

$R^1$ is selected from the group consisting of:
(1) $C_1$-$C_{10}$ alkyl, optionally substituted with 1 to 5 groups selected from the group consisting of:
 (a) hydroxy,
 (b) halogen,
 (c) cyano,
 (d) $QR^2$,
 (e) $C_3$-$C_8$ cycloalkyl,
 (f) $Q'COR^3$,
 (g) —$S(O)_p$—$NR^2R^2$,
 (h) —$N(R^2)SO_2R^3$, and
 (i) $Q'CO_2R^2$,
(2) $C_3$-$C_8$ cycloalkyl,
(3) oxo,
(4) halogen,
(5) cyano,
(6) $QR^2$,
(7) —$S(O)_p$—$NR^2R^2$,
(8) $Q'COR^3$,
(9) —$N(R^2)SO_2R^3$,
(10) $Q'CO_2R^2$, and
(11) Z, optionally substituted with 1 to 5 groups selected from the group consisting of:
 (a) $R^2$,
 (b) $QR^2$,
 (c) halogen, and
 (d) oxo;

$R^2$ is selected from the group consisting of:
(1) hydrogen,
(2) $C_1$-$C_{10}$ alkyl, optionally substituted with 1 to 5 groups selected from the group consisting of:
 (a) hydroxy,
 (b) halogen,
 (c) —$CO_2R^4$,
 (d) —$S(O)_p$—$C_1$-$C_{10}$ alkyl,
 (e) $C_3$-$C_8$ cycloalkyl,
 (f) $C_1$-$C_{10}$ alkoxy, optionally substituted with 1 to 5 halogens, and
 (g) Z, optionally substituted with 1 to 5 groups selected from the group consisting of halogen, trifluoromethyl, trifluoromethoxy, $C_1$-$C_{10}$ alkyl and $C_1$-$C_{10}$ alkoxy;
(3) $C_3$-$C_8$ cycloalkyl,
(4) Z, optionally substituted with 1 to 5 groups selected from the group consisting of:
 (a) halogen,
 (b) nitro,
 (c) oxo,
 (d) —$NR^4R^4$,
 (e) $C_1$-$C_{10}$ alkoxy, optionally substituted with 1 to 5 halogens,
 (f) —$S(O)_p$—$C_1$-$C_{10}$ alkyl, and
 (g) $C_1$-$C_{10}$ alkyl, optionally substituted with 1 to 5 groups selected from hydroxy, halogen, trifluoromethyl, cyano, —$CO_2R^4$, $C_3$-$C_8$ cycloalkyl, and $QR^5$;

$R^3$ is selected from the group consisting of:
(1) oxo,
(2) halogen,
(3) $R^2$, and
(4) —$NR^2R^2$;

$R^4$ is selected from the group consisting of:
(1) hydrogen, and
(2) $C_1$-$C_{10}$ alkyl;

$R^5$ is selected from the group consisting of:
(1) Z, optionally substituted with 1 to 5 groups selected from the group consisting of halogen, trifluoromethyl, cyano, $C_1$-$C_{10}$ alkyl, and $C_1$-$C_{10}$ alkoxy, and
(2) $C_1$-$C_{10}$ alkyl;

$R^6$ is selected from the group consisting of:
(1) hydrogen, and
(2) $C_1$-$C_{10}$ alkyl;

Q is selected from the group consisting of:
(1) —$N(R^2)$—,
(2) —O—, and
(3) —$S(O)_p$—; and Q' is selected from the group consisting of:
(1) —$N(R^2)$—,
(2) —O—, and
(3) a bond.

In one embodiment of Formula I, X is —CO— or —$SO_2$—. In one subset, X is —CO—. In another subset, X is —$SO_2$—.

In one embodiment of Formula I, Y is selected from the group consisting of:
(1) $C_1$-$C_3$ alkylene, optionally substituted with —$NR^2R^2$ or hydroxy,
(2) —$N(R^6)$—,
(3) —O—,
(4) a bond, and
(5) phenylene, optionally substituted with 1 to 3 groups independently selected from $R^1$.

In one subset of the above embodiment, Y is methylene, —$CH(CH_3)$— or a bond. In another subset, Y is methylene. In yet another subset, Y is a bond.

In one embodiment of Formula I, Z is selected from the group consisting of:
(1) phenyl,
(2) naphthyl,
(3) a 5- or 6-membered heterocyclic ring with from 1 to 4 heteroatoms selected from oxygen, sulfur and nitrogen,
(4) a benzene ring fused to a $C_5$-$C_{10}$ carbocyclic ring,
(5) a benzene ring fused to a 5- or 6-membered heterocyclic ring with from 1 to 4 heteroatoms selected from oxygen, sulfur and nitrogen,
(6) a 5- or 6-membered heterocyclic ring with from 1 to 4 heteroatoms selected from oxygen, sulfur and nitrogen fused to a 5- or 6-membered heterocyclic ring with from 1 to 4 heteroatoms selected from oxygen, sulfur and nitrogen, and
(7) a 5- or 6-membered heterocyclic ring with from 1 to 4 heteroatoms selected from oxygen, sulfur and nitrogen fused to a $C_5$-$C_{10}$ carbocyclic ring.

In one subset of the above embodiment, Z is selected from the group consisting of:
(1) phenyl,
(2) a 5-membered heterocyclic ring having one nitrogen atom and 0 to 3 additional heteroatoms independently selected from nitrogen, oxygen and sulfur,
(3) a 6-membered heterocyclic ring having 1, 2 or 3 nitrogen atoms, or 1 nitrogen atom and one oxygen or sulfur atom,
(4) a benzene ring fused to a 5- or 6-membered heterocyclic ring with from 1 to 4 heteroatoms selected from oxygen, sulfur and nitrogen,
(5) a benzene ring fused to a $C_5$-$C_{10}$ carbocyclic ring,
(6) a 5- or 6-membered heterocyclic ring with from 1 to 4 heteroatoms selected from oxygen, sulfur and nitrogen fused to a 5- or 6-membered heterocyclic ring with from 1 to 4 heteroatoms selected from oxygen, sulfur and nitrogen, and (7) a 5- or 6-membered heterocyclic ring with from 1 to 4 heteroatoms selected from oxygen, sulfur and nitrogen fused to a $C_5$-$C_{10}$ carbocyclic ring.

In another subset of the above embodiment, Z is phenyl.

In another subset of the above embodiment, Z is a benzene ring fused to a 5- or 6-membered heterocyclic ring with from 1 to 4 heteroatoms selected from oxygen, sulfur and nitrogen.

In another subset of the above embodiment, Z is selected from the group consisting of

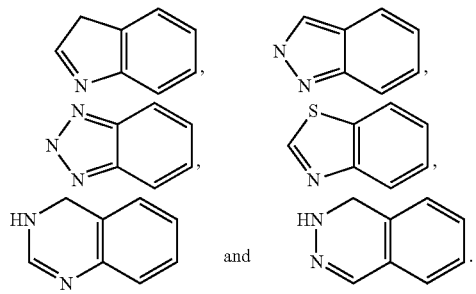

In another subset of the above embodiment, Z is a benzene ring fused to a $C_5$-$C_{10}$ carbocyclic ring.

In another subset of the above embodiment, Z is a 5- or 6-membered heterocyclic ring with from 1 to 4 heteroatoms selected from oxygen, sulfur and nitrogen. In one subset, Z is a 5-membered heterocycle having one nitrogen atom and 0 to 3 additional heteroatoms independently selected from N, O and S. In another subset Z is a 6-membered heterocycle having 1, 2 or 3 nitrogen atoms, or 1 nitrogen atom and an oxygen or sulfur atom. In yet another subset, Z is selected from the group consisting of thiazolyl, oxazolyl, pyridyl, dihydropyridyl, triazolyl (including 1,2,4-triazolyl and 1,2,3-triazolyl), tetrazolyl, pyrimidinyl, dihydropyrimidinyl, tetrahydropyrimidinyl, pyrazinyl, dihydropyrazinyl, pyridazinyl, dihydropyridazinyl, pyrrolidinyl, imidazolyl, pyrazolyl, and oxadiazolyl (including 1,2,4-oxadiazolyl and 1,2,5-oxadiazolyl). In one subset of this embodiment, Y is methylene. In another subset of this embodiment Y is a bond. In another subset of this embodiment Y is phenylene.

In another subset of the above embodiment, Z is a 5- or 6-membered heterocyclic ring with from 1 to 4 heteroatoms selected from oxygen, sulfur and nitrogen fused to a $C_5$-$C_{10}$ carbocyclic ring. In one subset the carbocyclic ring has 5 or 6 carbon atoms. In another subset the heterocycle is either a 5-membered heterocycle having one nitrogen atom and 0 to 3 additional heteroatoms independently selected from N, O and S, or a 6-membered heterocycle having 1, 2 or 3 nitrogen atoms, or 1 nitrogen atom and an oxygen or sulfur atom, and the carbocycle has 5 or 6 carbon atoms. In yet another subset Z is selected from the group consisting of: indolyl, benzimidazolyl, benzthiazolyl, quinolinyl, isoquinolinyl, tetrahydroquinolinyl, tetrahydroisoquinolinyl, chromenyl, benztriazolyl,

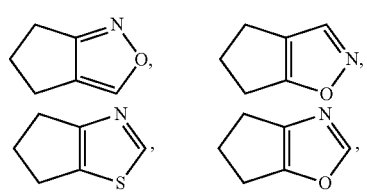

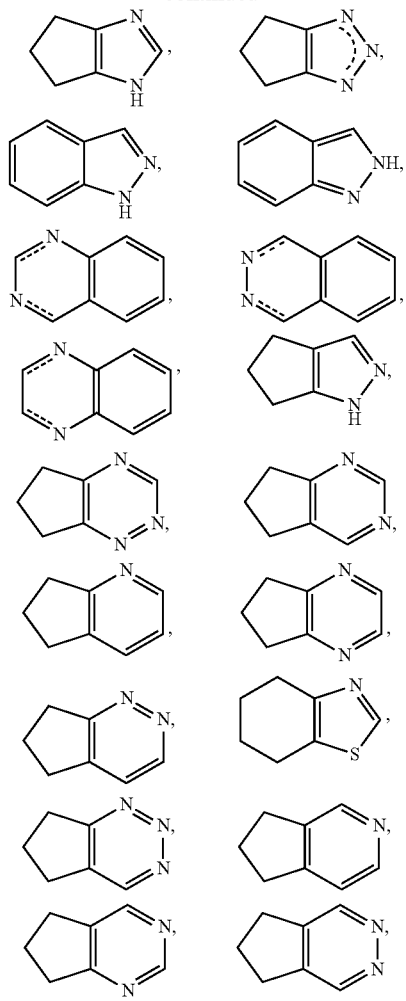

where the dash bond "----" means a single or double bond while conforming to the valency rule for the ring atoms. In one subset of this embodiment Y is methylene. In another subset of this embodiment Y is a bond.

In another subset of the above embodiment, Z is a 5- or 6-membered heterocyclic ring with from 1 to 4 heteroatoms selected from oxygen, sulfur and nitrogen fused to a 5- or 6-membered heterocyclic ring with from 1 to 4 heteroatoms selected from oxygen, sulfur and nitrogen. In one subset the fused ring has 2 to 5 heteroatoms, at least one of which is nitrogen. In another subset the fused ring has 2 to 4 nitrogen atoms and no other heteroatoms. In yet another subset the fused ring has one oxygen or sulfur atom, and 1 to 3 nitrogen atoms. In yet another subset, Z is selected from the group consisting of

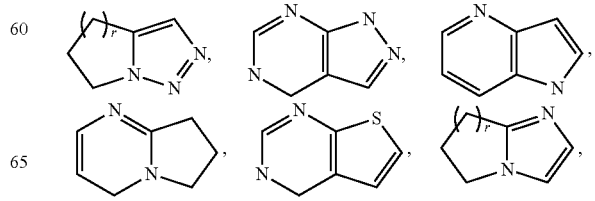

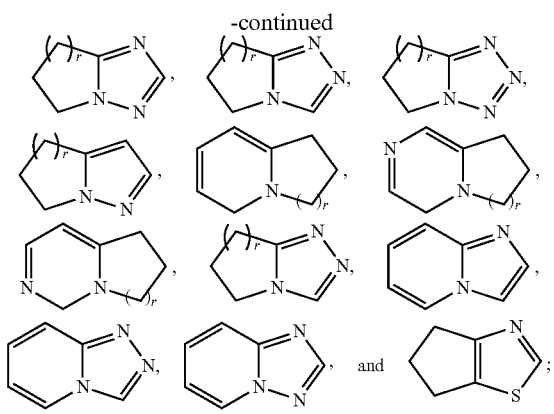

and wherein r is 1 or 2. In one subset of this embodiment Y is methylene. In another subset of this embodiment Y is a bond.

In one embodiment of Formula I, $R^1$ is selected from the group consisting of:
(1) $C_1$-$C_{10}$ alkyl, optionally substituted with 1 to 5 groups selected from the group consisting of:
  (a) hydroxy,
  (b) halogen,
  (c) cyano,
  (d) $QR^2$,
  (e) $C_3$-$C_8$ cycloalkyl,
  (f) $Q'COR^3$,
  (g) —$S(O)_p$—$NR^2R^2$,
  (h) —$N(R^2)SO_2R^3$, and
  (i) $Q'CO_2R^2$,
(2) $C_3$-$C_8$ cycloalkyl,
(3) oxo,
(4) halogen,
(5) cyano,
(6) $QR^2$,
(7) —$S(O)_p$—$NR^2R^2$,
(8) $Q'COR^3$,
(9) —$N(R^2)SO_2R^3$,
(10) $Q'CO_2R^2$, and
(11) Z, optionally substituted with 1 to 5 groups selected from the group consisting of:
  (a) $R^2$,
  (b) $QR^2$,
  (c) halogen, and
  (d) oxo;

In one subset of the above embodiment, $R^1$ is selected from the group consisting of:
(1) $C_1$-$C_6$ alkyl, optionally substituted with 1 to 5 groups selected from the group consisting of hydroxy and halogen,
(2) oxo,
(3) halogen,
(4) cyano, and
(5) $QR^2$.

In another subset of the above embodiment, $R^1$ is selected from the group consisting of:
(1) $C_1$-$C_4$ alkyl, optionally substituted with 1 to 5 groups selected from the group consisting of hydroxy and halogen,
(2) oxo, and
(3) halogen.

In one embodiment of Formula I, $R^2$ is selected from the group consisting of
(1) hydrogen,
(2) $C_1$-$C_{10}$ alkyl, optionally substituted with 1 to 5 groups selected from the group consisting of:
  (a) hydroxy,
  (b) halogen,
  (c) —$CO_2R^4$,
  (d) —$S(O)_p$—$C_1$-$C_{10}$ alkyl,
  (e) $C_3$-$C_8$ cycloalkyl,
  (f) $C_1$-$C_{10}$ alkoxy, optionally substituted with 1 to 5 halogens, and
  (g) Z, optionally substituted with 1 to 5 groups selected from the group consisting of halogen, trifluoromethyl, trifluoromethoxy, $C_1$-$C_{10}$ alkyl and $C_1$-$C_{10}$ alkoxy;
(3) $C_3$-$C_8$ cycloalkyl,
(4) Z, optionally substituted with 1 to 5 groups selected from the group consisting of:
  (a) halogen,
  (b) nitro,
  (c) oxo,
  (d) —$NR^4R^4$,
  (e) $C_1$-$C_{10}$ alkyl, optionally substituted with 1 to 5 halogens,
  (f) —$S(O)_p$—$C_1$-$C_{10}$ alkyl, and
  (g) $C_1$-$C_{10}$ alkyl, optionally substituted with 1 to 5 groups selected from hydroxy, halogen, trifluoromethyl, cyano, —$CO_2R^4$, $C_3$-$C_8$ cycloalkyl, and $QR^5$;

In another subset of the above embodiment, $R^2$ is selected from the group consisting of:
(1) hydrogen,
(2) $C_1$-$C_6$ alkyl, optionally substituted with 1 to 5 groups selected from the group consisting of hydroxy, halogen, and —$CO_2R^4$, and
(3) $C_3$-$C_8$ cycloalkyl.

In another subset of the above embodiment, $R^2$ is selected from the group consisting of:
(1) hydrogen, and
(2) $C_1$-$C_4$ alkyl, optionally substituted with 1 to 5 groups selected from the group consisting of hydroxy, halogen, and —$CO_2R^4$.

In one embodiment of Formula I, $R^3$ is selected from the group consisting of:
(1) oxo,
(2) halogen,
(3) $R^2$, and
(4) —$NR^2R^2$.

In one subset of the above embodiment, $R^3$ is selected from the group consisting of methyl, ethyl, propyl, isopropyl, trifluoromethyl, oxo, fluoro, chloro, and —$NH_2$.

In another subset of the above embodiment, $R^3$ is methyl or ethyl. In another embodiment, $R^3$ is fluoro or chloro. In another embodiment, $R^3$ is —$NH_2$. In yet another embodiment, $R^3$ is oxo.

In one embodiment of Formula I, $R^4$ is selected from the group consisting of:
(1) hydrogen, and
(2) $C_1$-$C_{10}$ alkyl.

In one subset of the above embodiment, $R^4$ is hydrogen or $C_1$-$C_{10}$ alkyl. In another subset, $R^4$ is hydrogen. In another subset, $R^4$ is methyl or ethyl.

In one embodiment of Formula I, $R^5$ is selected from the group consisting of:
(1) Z, optionally substituted with 1 to 5 groups selected from the group consisting of halogen, trifluoromethyl, cyano, $C_1$-$C_{10}$ alkyl, and $C_1$-$C_{10}$ alkoxy, and
(2) $C_1$-$C_{10}$ alkyl.

In one subset of the above embodiment, $R^5$ is selected from the group consisting of:
(1) phenyl, optionally substituted with 1 to 5 groups selected from the group consisting of halogen, trifluoromethyl, cyano, $C_1$-$C_{10}$ alkyl, and $C_1$-$C_{10}$ alkoxy, (2) a 5- or 6-membered heterocyclic ring with from 1 to 4 heteroatoms selected from oxygen, sulfur and nitrogen, (3) a benzene ring fused to a $C_5$-$C_{10}$ carbocyclic ring, (4) a benzene ring fused to a 5- or 6-membered heterocyclic ring with from 1 to 4 heteroatoms selected from oxygen, sulfur and nitrogen, and (5) $C_1$-$C_6$ alkyl.

In another subset of the above embodiment, $R^5$ is selected from the group consisting of:

(1) phenyl, optionally substituted with 1 to 5 groups selected from the group consisting of halogen, trifluoromethyl, cyano, $C_1$-$C_{10}$ alkyl, and $C_1$-$C_{10}$ alkoxy, (2) a 5- or 6-membered heterocyclic ring with from 1 to 4 heteroatoms selected from oxygen, sulfur and nitrogen, (3) a benzene ring fused to a 5- or 6-membered heterocyclic ring with from 1 to 4 heteroatoms selected from oxygen, sulfur and nitrogen, and (4) $C_1$-$C_4$ alkyl.

In one embodiment of Formula I, $R^6$ is selected from the group consisting of:

(1) hydrogen, and (2) $C_1$-$C_{10}$ alkyl.

In one subset of the above embodiment, $R^6$ is hydrogen or methyl.

In one embodiment of Formula I, m is 0, q is 0, and n is 0, 1 or 2.

In one subset of the above embodiment, X is —CO—. In another subset, X is —SO$_2$—.

In another subset, Y is methylene, —CH(CH$_3$)— or a bond.

In another subset, Z is phenyl.

In another subset, Z is a 5-membered heterocyclic ring having one nitrogen atom and 0 to 3 additional heteroatoms independently selected from N, O and S, or a 6-membered heterocycle having 1, 2 or 3 nitrogen atoms, or 1 nitrogen atom and one oxygen or sulfur atom.

In another subset, Z is selected from the group consisting of thiazolyl, oxazolyl, pyridyl, dihydropyridyl, 1,2,4-triazolyl, 1,2,3-triazolyl, tetrazolyl, pyrimidinyl, dihydropyrimidinyl, tetrahydropyrimidinyl, pyrazinyl, dihydropyrazinyl, pyridazinyl, dihydropyridazinyl, pyrrolidinyl, imidazolyl, pyrazolyl, 1,2,4-oxadiazolyl and 1,2,5-oxadiazolyl.

In another subset, Z is a 5- or 6-membered heterocyclic ring with from 1 to 4 heteroatoms selected from oxygen, sulfur and nitrogen fused to a $C_5$-$C_6$ carbocyclic ring, and wherein said heterocyclic ring is a 5-membered heterocycle having one nitrogen ring atom and 0 to 3 additional heteroatoms independently selected from N, O and S, or a 6-membered heterocycle having 1, 2 or 3 ring nitrogen atoms, or 1 ring nitrogen atom and a ring oxygen or sulfur atom.

In another subset, Z is selected from the group consisting of:

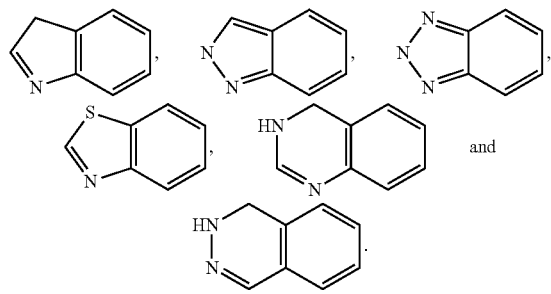

In another subset, $R^3$ is selected from the group consisting of:

(1) $C_1$-$C_6$ alkyl optionally substituted with 1 to 3 halogens, (2) oxo, (3) halogen, and (4) —NH$_2$.

In one embodiment of the compounds of Formula I are compounds of Formula Ia:

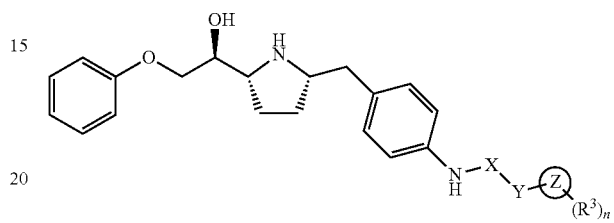

Ia wherein n is 0, 1 or 2;

X is —CO— or —SO$_2$—;

Y is selected from the group consisting of methylene, —CH(CH$_3$)—, and a bond;

Z is selected from the group consisting of a bond, phenyl, thiazolyl, pyridyl, dihydropyridyl, 1,2,4-triazolyl, pyrimidinyl, dihydropyrimidinyl, pyridazinyl, dihydropyridazinyl, pyrazolyl,

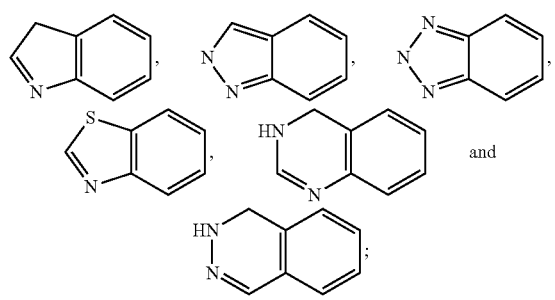

and $R^3$ is selected from the group consisting of:

(1) $C_1$-$C_6$ alkyl, optionally substituted with 1 to 3 halogens, (2) oxo, (3) Z, optionally substituted with 1 to 3 groups selected from the group consisting of halogen, —NH$_2$, $C_1$-C6 alkyl, and trifluoromethyl, and (4) —NR$^2$R$^2$, wherein each occurrence of R$^2$ is independently hydrogen or $C_1$-C6 alkyl.

In one subset of the above embodiment, n is 0 or 1.

In one subset of the above embodiment, $R^3$ is selected from the group consisting of:

(1) methyl, (2) oxo, (3) —NH$_2$, and (4) —NH—$C_1$-$C_6$ alkyl.

In another subset, Z is selected from the group consisting of:

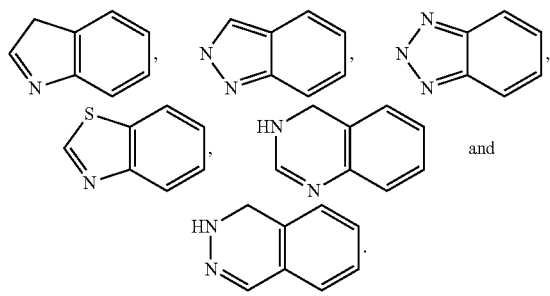

In another subset, Z is selected from the group consisting of phenyl, thiazolyl, pyridyl, dihydropyridyl, 1,2,4-triazolyl, pyrimidinyl, dihydropyrimidinyl, pyridazinyl, dihydropyridazinyl and pyrazolyl.

In another subset of the above embodiment, Y is methylene, —CH(CH$_3$)— or a bond. In one embodiment, Y is methylene. In another embodiment, Y is a bond.

In one embodiment, compounds of Formulas I and Ia have the specified stereoconfiguration at the indicated chiral center:

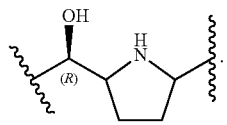

In another embodiment, compounds of Formulas I and Ia have the specified stereoconfiguration at the indicated chiral centers, with the chiral center marked with an asterisk being R or S:

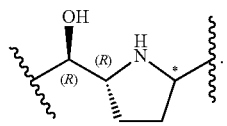

In one subset, the configuration at the chiral center marked with an asterisk is S. In another subset, the configuration at the chiral center marked with an asterisk is R.

As used herein "alkyl" is intended to include both branched- and straight-chain saturated aliphatic hydrocarbon groups having the specified number of carbon atoms, e.g., methyl (Me), ethyl (Et), n-propyl (Pr), n-butyl (Bu), n-pentyl, n-hexyl, and the isomers thereof such as isopropyl (i-Pr), isobutyl (i-Bu), secbutyl (s-Bu), tert-butyl (t-Bu), isopentyl, isohexyl and the like. "Cycloalkyl" means a monocyclic saturated carbocyclic ring, having the specified number of carbon atoms, e.g., 3, 4, 5 or 6 carbon atoms. Examples of cycloalkyl include cyclopropyl, cyclobutyl, cyclopentyl and cyclohexyl.

The term "optionally substituted" means "unsubstituted or substituted," and therefore, the generic structural Formulas described herein encompass compounds containing the specified optional substituent as well as compounds that do not contain the optional substituent. Each variable is independently defined each time it occurs within the generic structural formula definitions.

The terms "halo" or "halogen" are meant to include fluoro, chloro, bromo and iodo, unless otherwise noted. Fluoro and chloro are preferred.

The terms "carbocycle" or "carbocyclic" refer to saturated, partially unsaturated and aromatic rings having only ring carbon atoms. Examples include, but are not limited to cyclopentyl, cyclohexyl, cycloheptyl, cyclooctyl, cyclopentenyl, cyclohexenyl, cyclohexadienyl, and phenyl. The term "aryl" refers to an aromatic carbocycle. Within the definition for Z, the term "a benzene ring fused to a $C_5$-$C_{10}$ carbocyclic ring" includes, but is not limited to, naphthyl, dihydronaphthyl, tetrahydronaphthyl, indanyl, indenyl, benzocycloheptene, tetrahydrobenzocyloheptene, and the like; preferably benzene is fused to a $C_5$-$C_6$ carbocyclic ring. Such fused ring may be attached to the rest of the molecule via a carbon atom on either ring.

The terms "heterocycle" or "heterocyclic" refer to saturated, partially unsaturated and aromatic rings having at least one ring heteroatom and at least one ring carbon atom; the heterocycle may be attached to the rest of the molecule via a ring carbon atom or a ring nitrogen atom. The terms "heteroaryl" or "heteroaromatic" refer to an aromatic heterocycle. Within the definition for Z, the term "a 5- or 6-membered heterocyclic ring with from 1 to 4 heteroatoms selected from oxygen, sulfur and nitrogen" includes, but is not limited to, pyrrolyl, thienyl, furanyl, imidazoly, pyrazolyl, oxazolyl, isoxazolyl, thiazolyl, isothiazolyl, triazolyl, tetrazolyl, oxadiazolyl, thiadiazolyl, pyrrolidinyl, tetrahydrofuranyl, pyridinyl, dihydropyridinyl, tetrahydropyridinyl, pyrimidinyl, dihydropyrimidinyl, tetrahydropyrimidinyl, pyrazinyl, dihydropyrazinyl, tetrahydropyrazinyl, pyridazinyl, dihydropyridazinyl, tetrahydropyridazinyl, piperidinyl, piperazinyl, morpholinyl, pyranyl, dihydropyranyl, tetrahydropyranyl, and the like.

Within the definition for Z, the term "a 5- or 6-membered heterocyclic ring with from 1 to 4 heteroatoms selected from oxygen, sulfur and nitrogen fused to a 5- or 6-membered heterocyclic ring with from 1 to 4 heteroatoms selected from oxygen, sulfur and nitrogen" includes, but is not limited to, naphthyridinyl, dihydronaphthyridinyl, tetrahydronaphthyridinyl, imidazopyridinyl, pteridinyl, purinyl, quinolizinyl, indolizinyl, tetrahydroquinolizinyl, tetrahydroindolizinyl,

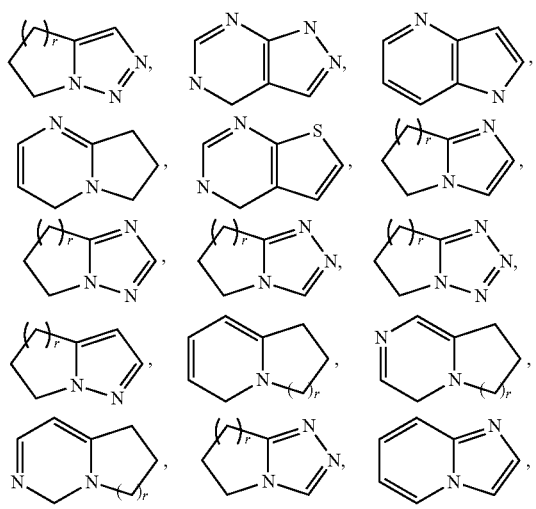

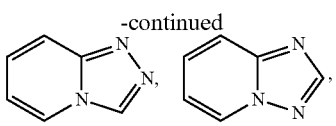

wherein r is 1 or 2. Such fused ring may be attached to the rest of the molecule via a carbon atom or a nitrogen atom on either ring. To avoid any doubt, the term "a 5- or 6-membered heterocyclic ring with from 1 to 4 heteroatoms selected from oxygen, sulfur and nitrogen fused to a 5- or 6-membered heterocyclic ring with from 1 to 4 heteroatoms selected from oxygen, sulfur and nitrogen" as used herein includes compounds having only one nitrogen as the sole heteroatom when the nitrogen is located at the bridgehead.

Within the definition for Z, the term "a 5- or 6-membered heterocyclic ring with from 1 to 4 heteroatoms selected from oxygen, sulfur and nitrogen fused to a $C_5$-$C_{10}$ carbocyclic ring" includes, but is not limited to, indolyl, isoindolyl, benzofuranyl, benzothienyl, benzimidazolyl, benzotriazolyl, benzoxazolyl, benzisoxazolyl, benzthiazolyl, benzisothiazolyl, quinolinyl, isoquinolinyl, quinoxalinyl, quinazolinyl, cinnolinyl, indazolyl, tetrahydroquinolinyl, tetrahydroindazolyl, dihydroindazolyl, chromenyl, chromanyl,

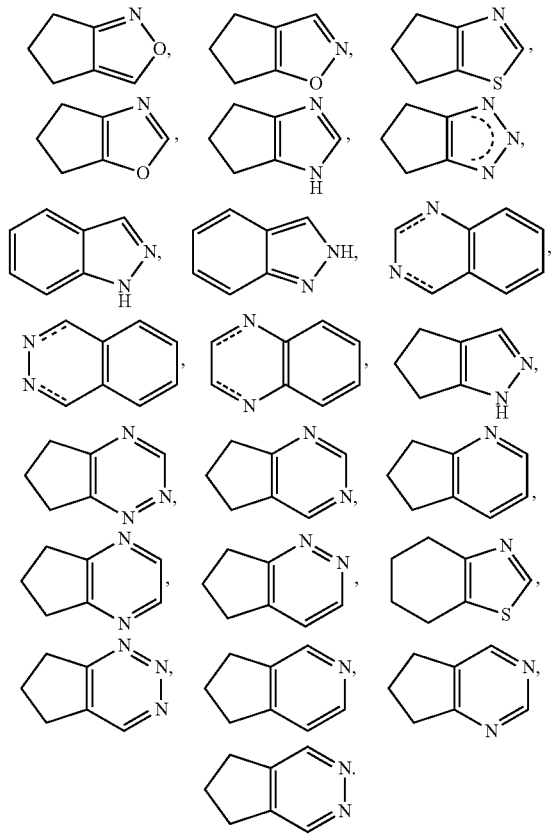

Such fused ring may be attached to the rest of the molecule via a carbon atom or a nitrogen atom on either ring.

For the terms $(R^1)_m$, $(R^2)_q$, $(R^3)_n$, as well as any other similar notations, when m or q or n is 0, then $R^1$, $R^2$ or $R^3$ is hydrogen; when m, q or n is greater than 1, then each occurrence of $R^1$, $R^2$ or $R^3$ is independently selected from other occurrences of $R^1$, $R^2$ or $R^3$, respectively. For example, when n is 2, the two $R^3$ substituents can be the same or different.

Optical Isomers—Diastereomers—Geometric Isomers—Tautomers

Compounds described herein may contain an asymmetric center and may thus exist as enantiomers. Where the compounds according to the invention possess two or more asymmetric centers, they may additionally exist as diastereomers. When bonds to the chiral carbon are depicted as straight lines in the formulas of the invention, it is understood that both the (R) and (S) configurations of the chiral carbon, and hence both enantiomers and mixtures thereof, are embraced within the formulas. The present invention includes all such possible stereoisomers as substantially pure resolved enantiomers, racemic mixtures thereof, as well as mixtures of diastereomers. The above Formulas I and Ia are shown without a definitive stereochemistry at certain positions. The present invention includes all stereoisomers of Formulas I and Ia and pharmaceutically acceptable salts thereof.

Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I or Ia may be obtained by stereospecific synthesis using optically pure starting materials or reagents of known configuration.

When compounds described herein contain olefinic double bonds, unless specified otherwise, such double bonds are meant to include both E and Z geometric isomers.

Some of the compounds described herein may exist with different points of attachment of hydrogen, referred to as tautomers. For example, compounds including carbonyl —$CH_2C(O)$— groups (keto forms) may undergo tautomerism to form hydroxyl —CH=C(OH)— groups (enol forms). Both keto and enol forms, individually as well as mixtures thereof, are included within the scope of the present invention.

Salts

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

Solvates

The present invention includes within its scope solvates of compounds of Formulas I and Ia. As used herein, the term "solvate" refers to a complex of variable stoichiometry formed by a solute (i.e., a compound of Formula I or Ia) or a pharmaceutically acceptable salt thereof and a solvent that does not interfere with the biological activity of the solute. Examples of solvents include, but are not limited to water, ethanol, and acetic acid. When the solvent is water, the solvate is known as hydrate; hydrates include, but are not limited to, hemi-, mono-, sesqui-, di- and tri-hydrates.

Prodrugs

The present invention includes within its scope the use prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with a compound of Formula I or Ia or with a compound which may not be a compound of Formula I or Ia, but which converts to a compound of Formula I or Ia in vivo after administration to the patient. Conventional procedures for the selection and preparation of suitable prodrug derivatives are described, for example, in "Design of Prodrugs," ed. H. Bundgaard, Elsevier, 1985.

Utilities

Compounds of the present invention are potent agonists of the β3-adrenoceptor, and as such are useful in treating or preventing diseases, disorders or conditions mediated by the activation of β3-adrenoceptor. Thus one aspect of the present invention provides a method for the treatment, control or prevention of such diseases, disorders, or conditions in a mammal which comprises administering to such mammal a therapeutically effective amount of a compound of Formula I or Ia. The term "mammal" includes human and non-human animals such as dogs and cats and the like. The diseases, disorders or conditions for which compounds of the present invention are useful in treating or preventing include, but are not limited to, (1) overactive bladder, (2) urinary incontinence, (3) urge urinary incontinence, (4) urinary urgency, (5) diabetes mellitus, (6) hyperglycemia, (7) obesity, (8) hyperlipidemia, (9) hypertriglyceridemia, (10) hypercholesterolemia, (11) atherosclerosis of coronary, cerebrovascular and peripheral arteries, (12) gastrointestinal disorders including peptic ulcer, esophagitis, gastritis and duodenitis, (including that induced by *H. pylori*), intestinal ulcerations (including inflammatory bowel disease, ulcerative colitis, Crohn's disease and proctitis) and gastrointestinal ulcerations, (13) neurogenic inflammation of airways, including cough, asthma, (14) depression, (15) prostate diseases such as benign prostate hyperplasia, (16) irritable bowel syndrome and other disorders needing decreased gut motility, (17) diabetic retinopathy, (18) preterm labor, and (19)-elevated intraocular pressure and glaucoma.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formulas I and Ia are administered orally.

The effective dosage of active ingredient employed may vary depending on the particular compound employed, the mode of administration, the condition being treated and the severity of the condition being treated. Such dosage may be ascertained readily by a person skilled in the art.

When treating overactive bladder (OAB) in conjunction with other anti-OAB agents, or alone, generally satisfactory results are obtained when the compounds of the present invention are administered at a daily dosage of from 0.01 milligram to about 100 milligrams per kilogram of animal body weight, preferably given in a single dose or in divided doses two to six times a day, or in sustained release form. In the case of a 70 kg adult human, the total daily dose will generally be from about 0.7 milligrams to about 3500 milligrams, or more specifically, from about 0.7 milligrams to about 2000 milligrams. This dosage regimen may be adjusted to provide the optimal therapeutic response.

When treating obesity, in conjunction with diabetes and/or hyperglycemia, or alone, generally satisfactory results are obtained when the compounds of the present invention are administered at a daily dosage of from 0.01 milligram to about 100 milligrams per kilogram of animal body weight, preferably given in a single dose or in divided doses two to six times a day, or in sustained release fowl. In the case of a 70 kg adult human, the total daily dose will generally be from about 0.7 milligrams to about 3500 milligrams. This dosage regimen may be adjusted to provide the optimal therapeutic response.

When treating diabetes mellitus and/or hyperglycemia, as well as other diseases or disorders for which compounds of Formulas I and Ia are useful, generally satisfactory results are obtained when the compounds of the present invention are administered at a daily dosage of from about 0.001 milligram to about 100 milligram per kilogram of animal body weight, preferably given in a single dose or in divided doses two to six times a day, or in sustained release form. In the case of a 70 kg adult human, the total daily dose will generally be from about 0.07 milligrams to about 350 milligrams. This dosage regimen may be adjusted to provide the optimal therapeutic response.

In one embodiment, a compound of the present invention is used in the manufacture of a medicament for the treatment or prevention of a disease or disorder mediated by the activation of β3-adrenoceptor.

Another aspect of the present invention provides pharmaceutical compositions which comprises a compound of Formula I or Formula Ia and a pharmaceutically acceptable carrier. The pharmaceutical compositions of the present invention comprise a compound of Formula I or Ia as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, intravesical, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formulas I and Ia can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of Formulas I and Ia may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Compounds of Formulas I and Ia may be used in combination with other drugs that are used in the treatment/prevention/suppression or amelioration of the diseases or conditions for which compounds of Formulas I and Ia are useful. Such other drugs may be administered, by a route and in an amount commonly used therefor, contemporaneously or sequentially with a compound of Formula I or Ia. When a compound of Formula I or Ia is used contemporaneously with one or more other drugs, a pharmaceutical unit dosage form containing such other drugs in addition to the compound of Formula I or Ia is preferred. Accordingly, the pharmaceutical compositions of the present invention include those that also contain one or more other active ingredients, in addition to a compound of Formula I or Ia. Examples of other active ingredients that may be combined with a compound of Formula I or Ia, either administered separately or in the same pharmaceutical compositions, include, but are not limited to:

(a) overactive bladder medicines including (i) muscarinic receptor antagonists (e.g. tolterodine, oxybutynin including S-oxybutynin, hyoscyamine, propantheline, propiverine, trospium including trospium chloride, solifenacin, darifenacin, imidafenacin, fesoterodine, temiverine, SVT-40776, 202405 by GlaxoSmithKline, TD6301, RBX9841, DDP200, PLD179, and other anticholinergics. See, for example, U.S. Pat. Nos. 5,382,600; 3,176,019; 3,480,626; 4,564,621; 5,096, 890; 6,017,927; 6,174,896; 5,036,098; 5,932,607; 6,713,464; 6,858,650; and DD 106643. See also, U.S. Pat. Nos. 6,103, 747; 6,630,162; 6,770,295; 6,911,217; 5,164,190; 5,601,839; 5,834,010; 6,743,441; WO2002000652; WO200400414853. As will be appreciated by those of skill in the art, these drugs may be administered orally or topically in standard or extended release forms, such as extended release talterodine, extended release oxybutynin and transdermal oxybutynin), (ii) NK-1 or NK-2 antagonists (e.g. aprepitant, cizolirtine, compounds disclosed in WO2005/073191, WO2005/032464, and other reported NK-1 antagonists), (iii) alpha adrenergic receptor antagonists (e.g. alfuzosin, doxazosin, prazosin, tamsulosin, terazosin, and others), (iv) potassium channel openers (e.g. cromakalim, pinacidil, and others), (v) vanilloids and other afferent-nerve modulators—agonists and antagonists (e.g. capsaicin, resiniferatoxin, and others), (vi) dopamine D1 receptor agonists (e.g. pergolinde), (vii) serotonergic and/or norepinephrine reuptake inhibitors (e.g. duloxetine), (viii) neuromuscular junction inhibition of acetylcholine release (e.g. botulinum toxin), (ix) calcium channel blockers (e.g. diltiazem, nifedipine, verapamil, and others), (x) inhibitors of prostaglandin synthesis (e.g. flurbiprofen), (xi) gamma aminobutyric acid receptor antagonists (e.g. baclofen), (xii) vaginal estrogen preparations (xiii) selective norepinephrine reuptake inhibitors, (xiv) 5-HT2C agonists, (xv) voltage gated sodium channel blacker, (xvi) P2X purinergic receptor antagonists (e.g. P2X1 or P2X3 antagonists), (xvii) PAR2 inhibitors, (xviii) phosphodiesterase inhibitors (e.g. PDE1, PDE4, and PDE5 inhibitors); and (xix) ATP sensitive potassium channel openers.

(b) insulin sensitizers including (i) PPARγ agonists such as the glitazones (e.g. troglitazone, pioglitazone, englitazone, MCC-555, BRL49653 and the like), and compounds disclosed in WO97/27857, 97/28115, 97/28137 and 97/27847; (ii) biguanides such as metformin and phenformin;

(c) insulin or insulin mimetics;

(d) sulfonylureas such as tolbutamide and glipizide;

(e) α-glucosidase inhibitors (such as acarbose), (f) cholesterol lowering agents such as (i) HMG-CoA reductase inhibitors (lovastatin, simvastatin and pravastatin, fluvastatin, atorvastatin, and other statins), (ii) sequestrants (cholestyramine, colestipol and a dialkylaminoalkyl derivatives of a cross-linked dextran), (ii) nicotinyl alcohol nicotinic acid or a salt thereof, (iii) proliferator-activater receptor α agonists such as fenofibric acid derivatives (gemfibrozil, clofibrat, fenofibrate and benzafibrate), (iv) inhibitors of cholesterol absorption for example beta-sitosterol and ezetimibe, and (acyl CoA:cholesterol acyltransferase) inhibitors for example melinamide, (v) probucol, (vi) vitamin E, and (vii) thyromimetics;

(g) PPARδ agonists such as those disclosed in WO97/28149;

(h) antiobesity compounds such as fenfluramine, dexfenfluramine, phentermine, sibutramine, orlistat, and other $β_3$ adrenergic receptor agonists;

(i) feeding behavior modifying agents such as neuropeptide Y antagonists (e.g. neuropeptide Y5) such as those disclosed in WO 97/19682, WO 97/20820, WO 97/20821, WO 97/20822 and WO 97/20823;

(j) PPARα agonists such as described in WO 97/36579 by Glaxo;

(k) PPARγ antagonists as described in WO97/10813; and (l) serotonin reuptake inhibitors such as fluoxetine and sertraline.

In one embodiment, a compound of the present invention and a second active agent as described above are used in the manufacture of a medicament for the treatment or prevention of a disease or disorder mediated by the activation of β3-adrenoceptor.

The compounds of Formula I and Ia of the present invention can be prepared according to the procedures of the following Schemes and Examples using appropriate materials, and are further exemplified by the following specific examples. Moreover, by utilizing the procedures described herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogen carbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless otherwise noted. Mass spectra (MS) were measured by electron-spray ion-mass spectroscopy.

A variety of chromatographic techniques may be employed in the preparation of the compounds. These techniques include, but are not limited to: High Performance Liquid Chromatography (HPLC) including normal phase, reversed phase, and chiral phase HPLC; Medium Pressure Liquid Chromatography (MPLC), Super Critical Fluid Chromatography; preparative Thin Layer Chromatography (prep TLC); flash chromatography with silica gel or reversed-phase silica gel; ion-exchange chromatography; and radial chromatography. All temperatures are degrees Celsius unless otherwise noted.

The phrase "standard peptide coupling reaction conditions" means coupling a carboxylic acid with an amine using an acid activating agent such as EDC, DCC, and BOP in an inert solvent such as dichloromethane in the presence of a catalyst such as HOBT and HOAT. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., *Protective Groups in Organic Synthesis*, John Wiley & Sons, Inc., New York, N.Y., 1991. MOZ and BOC are commonly used protecting groups in organic synthesis, and their removal conditions are known to those skilled in the art. For example, MOZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of MOZ groups can also be achieved by treatment with a solution of trifluoroacetic acid, hydrochloric acid or hydrogen chloride gas, in a solvent such as dichloromethane, methanol, or ethyl acetate. Removal of BOC protecting groups is carried out with a strong acid, such as trifluoroacetic acid, hydrochloric acid, or hydrogen chloride gas, in a solvent such as dichloromethane, methanol, or ethyl acetate.

Throughout the application, the following terms have the indicated meanings unless otherwise noted:

| Term | Meaning |
| --- | --- |
| Bn | Benzyl |
| BOC (Boc) | t-Butyloxycarbonyl |
| ° C. | Degree Celsius |
| Calc. or calc'd | Calculated |
| Celite | Celite ™ diatomaceous earth |
| EDC | 1-Ethyl-3-(3-dimethylaminopropyl) carbodiimide |
| Et | Ethyl |
| EtOAc | Ethyl acetate |
| EtOH | Ethanol |
| g | Gram(s) |
| h or hr | Hour(s) |
| HOBt | 1-Hydroxybenzotriazole |
| HPLC | High performance liquid chromatography |
| LC/MS or LC-MASS | Liquid chromatography mass spectrum |
| L | Liter(s) |
| M | Molar(s) |
| Me | Methyl |
| min | Minute(s) |
| mg | Milligram(s) |
| mL | Milliliter(s) |
| mmol | Millimole(s) |
| MS | Mass spectrum |
| Ph | Phenyl |
| Ref. | Reference |
| r.t. or rt | Room temperature |
| Sat. | Saturated |
| TBAF | Tetrabutylammonium fluoride |
| TBS, TBDMS | Tert-butyl dimethylsilyl |
| TEA or Et$_3$N | Triethylamine |
| TFA | Trifluoroacetic acid |
| THF | Tetrahydrofuran |
| TLC | Thin-layer chromatography |
| TMS | Trimethylsilyl |

Reaction Schemes below illustrate the methods employed in the synthesis of the compounds of the present invention of Formula I. All substituents are as defined above unless indicated otherwise. The synthesis of the novel compounds of Formula I which are the subject of this invention may be accomplished by one or more of several similar routes.

Scheme I

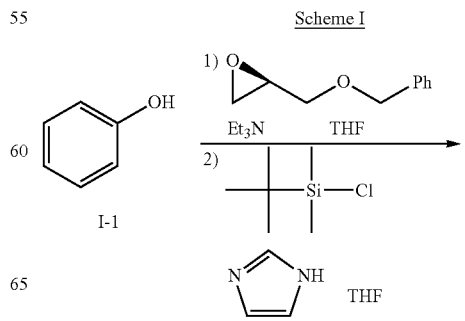

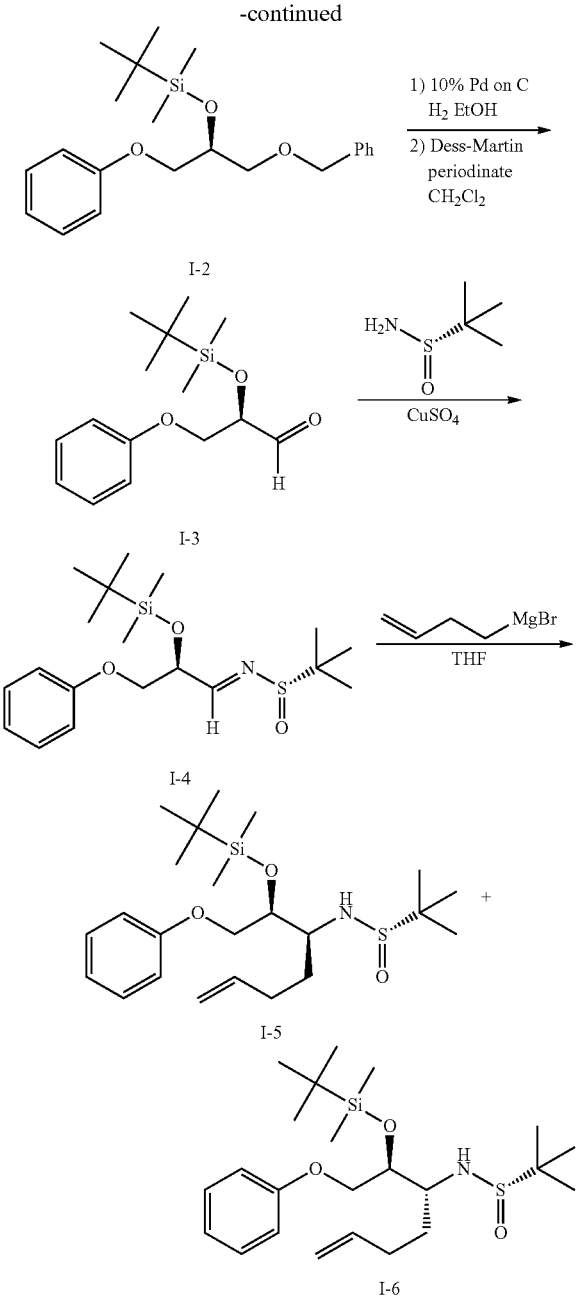

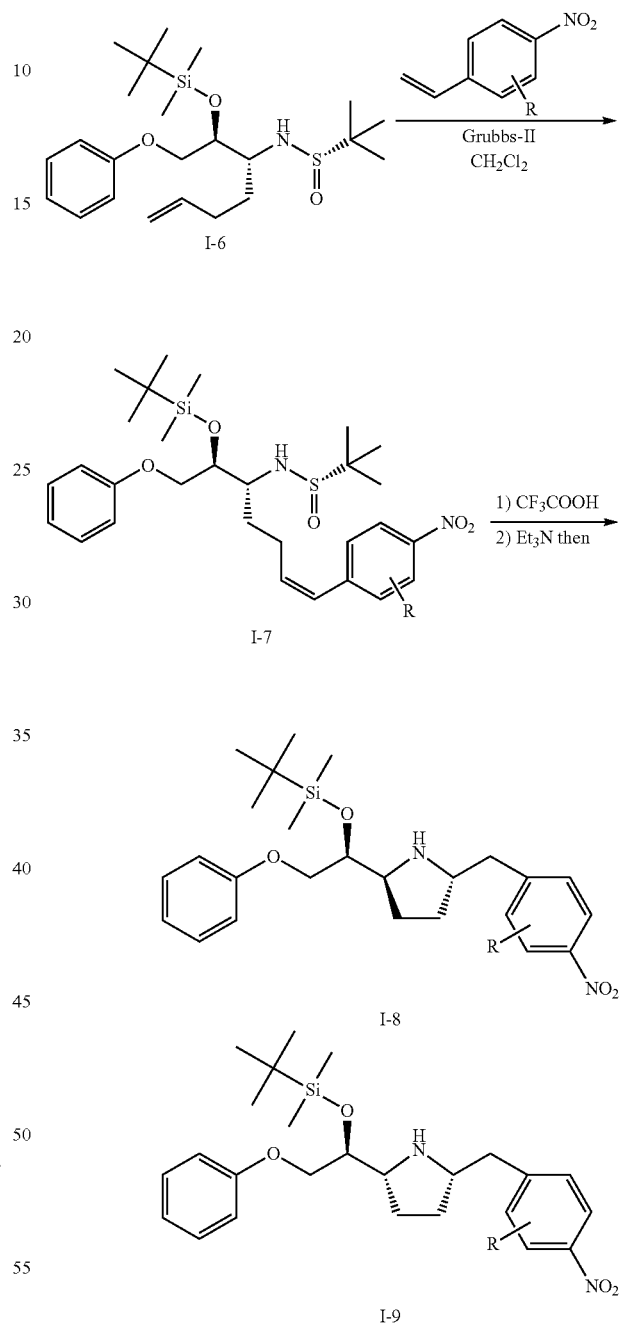

In Scheme I, an appropriately substituted phenol I-1 can be reacted with (R)-(−)-benzyl glycidyl ether in the presence of a catalytic amount of an organic base such as triethylamine at 40° C. for 12-18 hours from which the epoxide ring-opened product may be obtained. This secondary alcohol product may be protected by adding tert-butyldimethylsilyl chloride in the presence of an organic base such as imidazole or trialkylamine at room temperature for 12-16 hours to afford the silylated ether I-2. The reaction is usually performed in an inert organic solvent such as THF under an inert atmosphere such as nitrogen.

The benzyl group may then be removed. Treatment of silyl ether I-2 as an alcohol solution, for example ethyl alcohol, with hydrogen gas over a hydrogenation catalyst such as 10% palladium on carbon, at room temperature over a period of 2 hours yields the primary alcohol. The alcohol may be converted to the aldehyde I-3 by an oxidation reaction with an oxidizing agent such as Dess-Martin periodinate in a chlorinated solvent such as methylene chloride. Conversion of the aldehyde to the sulfinylimine I-4 may be effected with (S)-tert-butylsulfinylamide in the presence of a dehydrating agent such as anhydrous copper(II) sulfate. The resulting amine can then be reacted with 3-butenylmagnesium bromide in THF or methylene chloride to afford a mixture of diastereomeric compounds I-5 and I-6 that may be separated by those skilled in the art of chromatography.

In Scheme II, reaction of the sulfinimine I-6 in methylene chloride with an appropriately substituted 4-nitrostyrene and an olefin metathesis catalyst, for example, Grubbs type-II catalyst, leads to the formation of I-7. Removal of sulfinyl group may be effected with an acid, such as trifluoroacetic acid, in an inert organic solvent, for example, methylene chloride, and when this is followed with the treatment with a trialkylamine organic base, such as triethyl amine, the intermediate ring closes to afford a mixture of the cis and trans 2,5-substituted pyrrolidine derivatives I-8 and I-9.

Scheme III

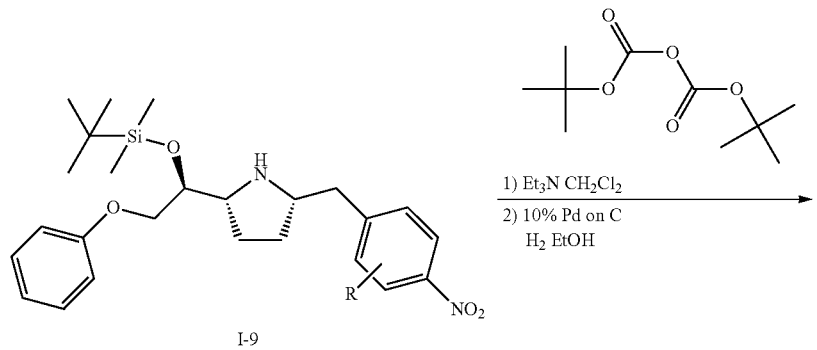

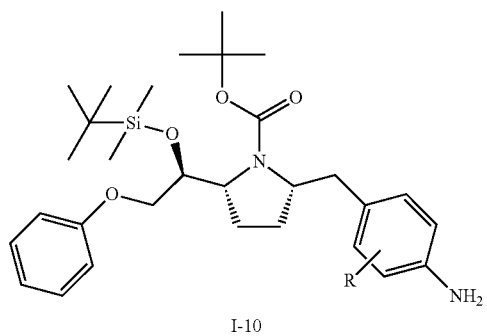

In Scheme III, using di-tert-butyldicarbonate in an inert organic solvent, such as methylene chloride, the nitrogen of the cis 1,5-disubstituted pyrrolide 1-9 may be derivatized to give a N-Boc protected carbamate. Catalytic hydrogenation of this intermediary Boc-compound in an alcohol solvent, for example ethyl alcohol, with hydrogen gas in the presence of a hydrogenation catalyst such as 10% palladium on carbon, at room temperature for a period of 2 to 4 hours converts the nitrophenyl group into the corresponding aniline I-10.

Scheme IV

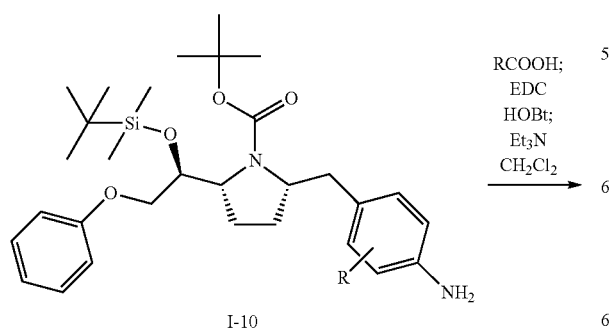

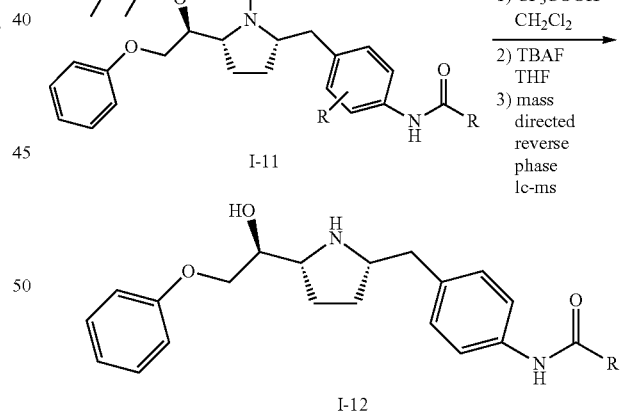

In Scheme IV, the aniline I-10 can be converted into the amide derivative I-11 by a reaction with an appropriate acid in an organic solvent such as methylene chloride with a carbodiimide such as EDC with HOBt in the presence of a trialkylamine for example triethylamine. Removal of the Boc- and TBS-protecting groups from amide I-11 may be achieved by sequential reaction with an acid to remove the Boc group and then removal of the silicon protecting group with an organic fluoride, such as tributylammonium fluoride in an ethereal solvent such as tetrahydrofuran. This leads to the cis-2,5-disubstituted pyrrolidine compound I-12.

Scheme V

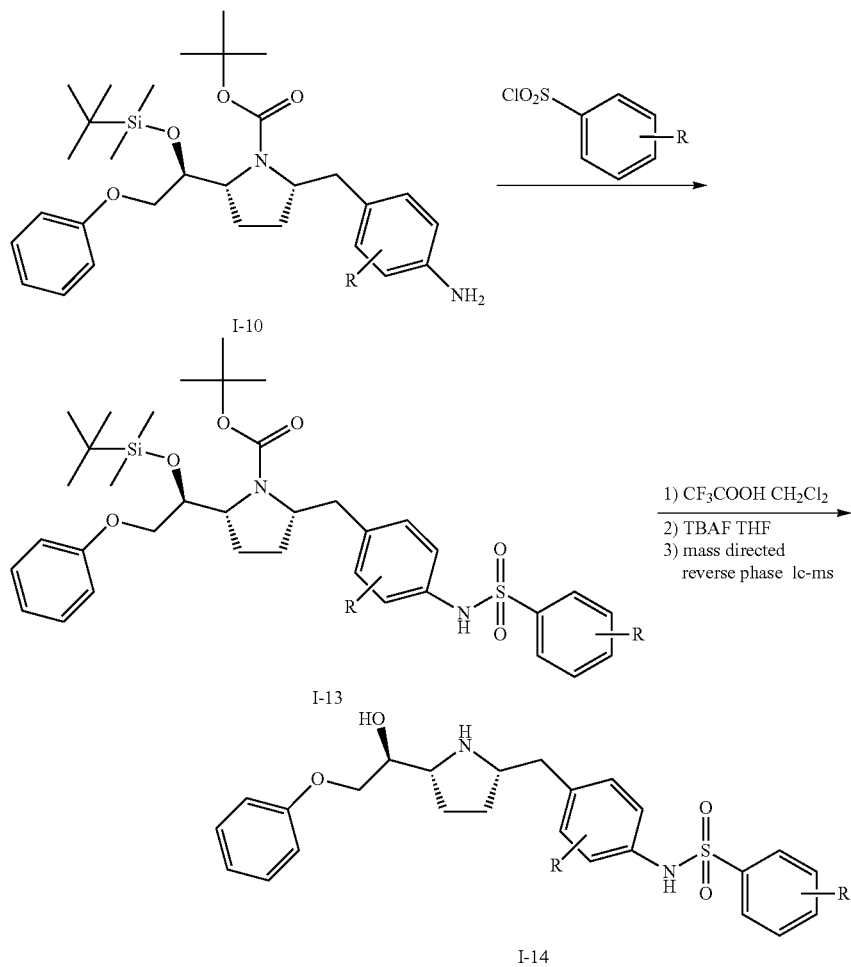

In Scheme V, the aniline I-10 can be converted into sulfonamide derivative I-13 with appropriate sulfonyl chloride in an organic solvent such as methylene chloride in the presence of a trialkylamine for example triethylamine. Removal of the Boc- and TBS-protecting groups from the sulfonamide derivative I-13 may be achieved by sequential reaction with an acid to remove the Boc group and then removal of the silicon protecting group with an organic fluoride, such as tributylammonium fluoride in an ethereal solvent such as tetrahydrofuran and this affords to the cis-2,5-disubstituted pyrrolidine compound I-12.

Scheme VI

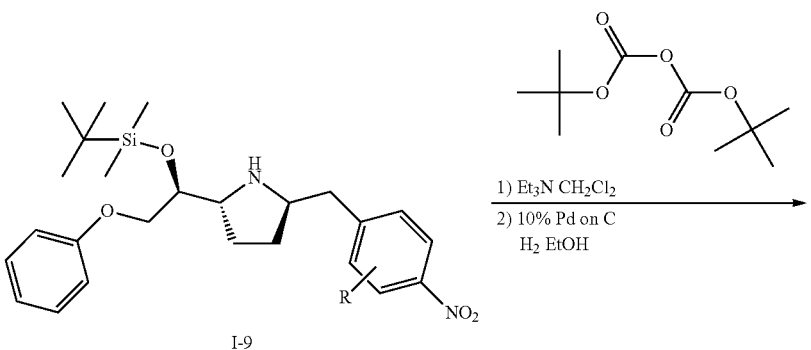

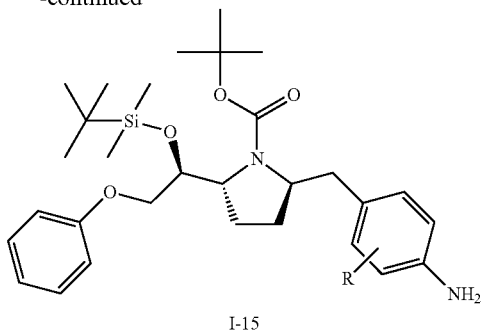

I-15

In Scheme VI, in a similar manner to the method described above for the cis-pyrrolidine, trans-2,5-substituted pyrrolidine 1-9 may be reacted with di-tert-butyldicarbonate in an inert organic solvent, such as methylene chloride, to give a trans 1,5-disubstituted pyrrolidine as its N-Boc protected carbamate. The corresponding aniline I-15 may be obtained by catalytic hydrogenation of the nitro group of this intermediary Boc-protected compound in an alcohol solvent, for example ethyl alcohol, in the presence of a catalyst such as 10% palladium on carbon, at room temperature for a period of 2 to 4 hours.

Scheme VII

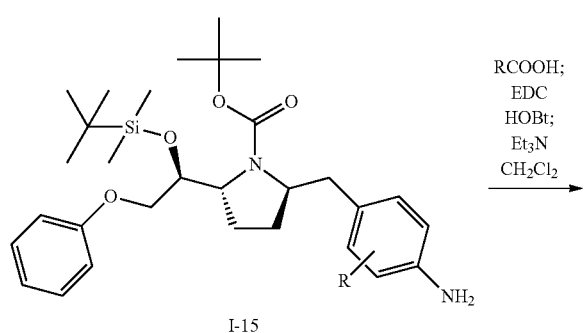

I-15

RCOOH;
EDC
HOBt;
Et₃N
CH₂Cl₂ →

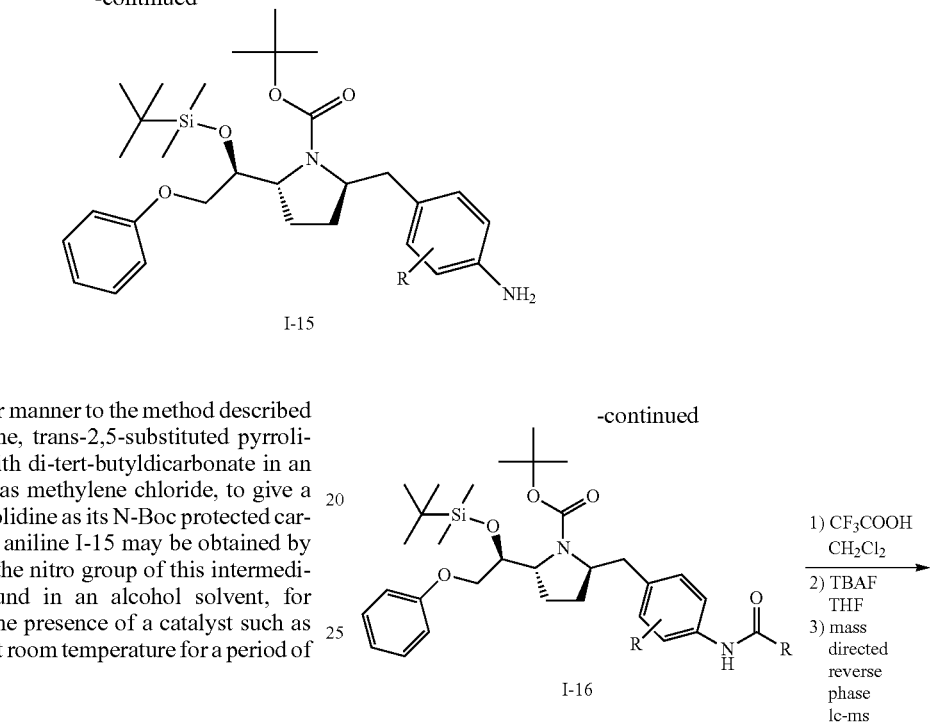

1) CF₃COOH CH₂Cl₂
2) TBAF THF
3) mass directed reverse phase lc-ms

I-16

I-17

In Scheme VII, the aniline I-15 can be converted into the amide derivative I-16 by the reaction with an appropriate acid in an organic solvent such as methylene chloride and a carbodi-imide such as EDC in the presence of HOBt and a trialkylamine for example triethylamine. Deprotection of amide I-16 may be achieved by sequential reaction with an acid to remove the Boc group and then removal of the silicon group with an organic fluoride, such as tributylammonium fluoride in an ethereal solvent such as tetrahydrofuran. This leads to the cis-2,5-disubstituted pyrrolidine compound I-17 after purification by mass directed LC-MS.

Scheme VIII

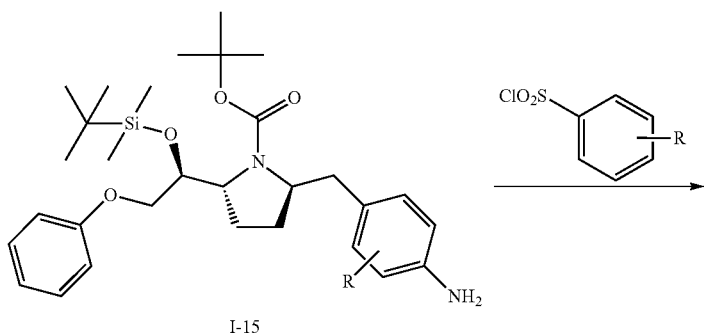

I-15

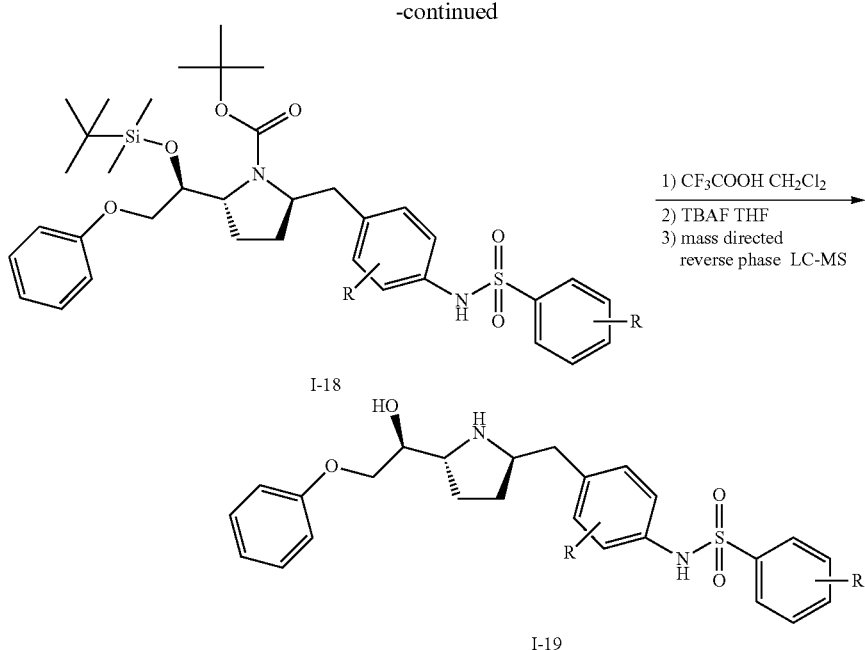

I-18

I-19

In Scheme VII, the aniline I-15 in a similar manner to that described above can be converted into sulfonamide derivative I-18 with appropriate sulfonyl chloride in a suitable organic solvent such as methylene chloride in the presence of a trialkylamine for example triethylamine. Removal of the Boc- and TBS-protecting groups from sulfonamide derivative I-18 may be achieved by sequential reaction with an acid to remove the Boc group and then removal of the silicon protecting group with an organic fluoride, such as tributylammonium fluoride in an ethereal solvent such as tetrahydrofuran and this affords to the cis-2,5-disubstituted pyrrolidine compound I-19.

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

Biological Assays

The following in biological assays are suitable for screening compounds that have selective β3 agonist activity:

Functional Assay: cAMP production in response to ligand is measured according to Barton et al (1991, Agonist-induced desensitization of D2 dopamine receptors in human Y-79 retinoblastoma cells. Mol. Pharmacol. v3229:650-658) modified as follows. cAMP production is measured using a homogenous time-resolved fluorescence resonance energy transfer immunoassay (LANCE™, Perkin Elmer) according to the manufacture's instructions. Chinese hamster ovary (CHO) cells, stably transfected with the cloned β-adrenergic receptor (β1, β2 or β3) are harvested after 3 days of subculturing. Harvesting of cells is done with Enzyme-free Dissociation Media (Specialty Media). Cells are then counted and resuspended in assay buffer (Hank's Balanced salt solution supplemented with 5 mM HEPES, 0.1% BSA) containing a phosphodiesterase inhibitor (IBMX, 0.6 mM). The reaction is initiated by mixing 6,000 cells in 6 μL with 6 μL Alexa Fluor labeled cAMP antibody (LANCE™ kit) which is then added to an assay well containing 12 ul of compound (diluted in assay buffer to 2× final concentration). The reaction proceeds for 30 minutes at room temperature and is terminated by the addition of 24 μL detection buffer (LANCE™ kit). The assay plate is then incubated for 1 hour at room temperature and time-resolved fluorescence measured on a Perkin Elmer Envision reader or equivalent. The unknown cAMP level is determined by comparing fluorescence levels to a cAMP standard curve.

The non-selective, full agonist β-adrenergic ligand isoproterenol is used at all three receptors to determine maximal stimulation. The human β3 adrenergic receptor (AR) selective ligand (S)—N-[4-[2-[[2-hydroxy-3-(4-hydroxyphenoxy)propyl]amino]ethyl]-phenyl]-4-iodobenzenesulfonamide is used as a control in all assays. Isoproterenol is titrated at a final concentration in the assay of $10^{-10}$ M to $10^{-5}$ M and the selective ligand (S)—N-[4-[2-[[2-hydroxy-3-(4-hydroxyphenoxy)propyl]amino]ethyl]phenyl]-4-iodobenzene-sulfonamide is titrated at the β3 receptor at concentration of $10^{-10}$ M to $10^{-5}$ M. Unknown ligands are titrated at all 3 β-adrenergic receptor subtypes at a final concentration in the assay of $10^{-10}$ M to $10^{-5}$ M to determine the $EC_{50}$. The $EC_{50}$ is defined as the concentration of compound that gives 50% activation of its own maximum. Data are analyzed using Microsoft Excel and Graphpad Prism or an internally developed data analysis software package.

Binding Assay: Compounds are also assayed at the β1 and β2 receptors to determine selectivity. All binding assays are run using membranes prepared from CHO cells recombinantly expressing β1 or β2 receptors. Cells are grown for 3-4 days post splitting; the attached cells are washed with PBS and then lysed in 1 mM Tris, pH 7.2 for 10 minutes on ice. The flasks are scraped to remove the cells and the cells then homogenized using a Teflon/glass homogenizer. Membranes are collected by centrifuging at 38,000×g for 15 minutes at 4° C. The pelleted membranes are resuspended in TME buffer (50 mM Tris, pH 7.4, 5 mM $MgCl_2$, 2 mM EDTA) at a concentration of 1 mg protein/ml. Large batches of membranes can be prepared, aliquoted and stored at −70° C. for up to a year without loss of potency. The binding assay is performed by incubating together membranes (2-5 μg of protein), the radiolabelled tracer $^{125}$I-cyanopindolol ($^{125}$I-CYP, 45 pM), 200 μg of WGA-PVT SPA beads (GE Healthcare) and the test compounds at final concentrations ranging from $10^{-10}$ M to $10^{-5}$ M in a final volume of 200 μL of TME buffer containing 0.1% BSA. The assay plate is incubated for 1 hour with shaking at room temperature and then placed in a Perkin Elmer Trilux scintillation counter. The plates are allowed to rest in the Trilux counter for approximately 10 hours in the dark prior to counting. Data are analyzed using a standard 4-parameter non-linear regression analysis using either Graphpad Prism software or an internally developed data analysis package. The $IC_{50}$ is defined as the concentration of the compound capable of inhibiting 50% of the binding of the radiolabelled tracer ($^{125}$I-CYP). A compound's selectivity for the β3 receptor may be determined by calculating the ratio ($IC_{50}$ β1 AR, β2 AR)/($EC_{50}$ β3 AR).

EXAMPLE 1

2-(2-Amino-1,3-thiazol-4-yl)-N-[4-({(2S,5R)-5-[(1S)-1-hydroxy-2-phenoxyethyl]pyrrolidin-2-yl}methyl)phenyl]acetamide bis-trifluoroacetate salt

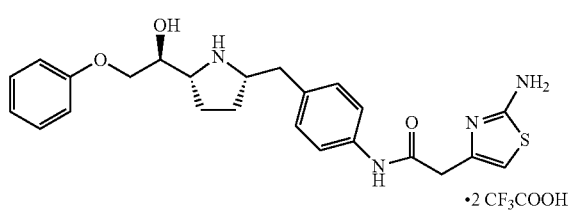 [SMILES: Nc1nc(CC(=O)Nc2ccc(C[C@@H]3CC[C@H]([C@H](O)COc4ccccc4)N3)cc2)cs1]

Step A: Preparation of (2S)-1-(benzyloxy)-3-phenoxypropan-2-ol

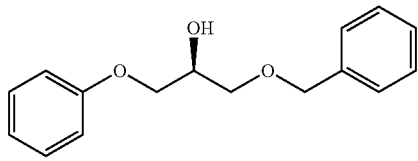 [SMILES: O[C@@H](COCc1ccccc1)COc1ccccc1]

A solution of phenol (3.3 g; 35 mmol), benzyl(R)-(+)-glycidyl ether (5 g; 30.5 mmol) and triethylamine (300 μl; 2.15 mmol) in absolute ethanol (80 ml) was heated to reflux and stirred for 2 hours and then cooled to 60° C. and stirred overnight. The crude reaction mixture was concentrated under reduced pressure and the residues purified by silica gel chromatography using an eluant of hexanes and ethyl acetate (85:15 v/v) to afford 5.7 g (72.5%) of the pure product. m/z (ES) 281.1 (M+Na)$^+$.

Step B: Preparation of [(1S)-2-(benzyloxy)-1-(phenoxymethyl)ethoxy](tert-butyl)dimethylsilane

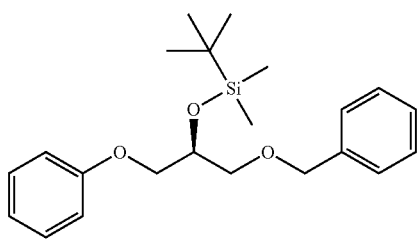 [SMILES: CC(C)(C)[Si](C)(C)O[C@@H](COCc1ccccc1)COc1ccccc1]

The alcohol (5.4 mg; 20.9 mmol) from Step A in methylene chloride (100 ml) was stirred at 0° C. Triethylamine (3.5 ml; 25.1 mmol) was added to the solution and followed with t-butyldimethylsilyl trifluoromethanesulfonate (5.8 g; 21.95 mmol). The reaction mixture was stirred at 0° C. for 1 hour, then quenched by the addition of saturated aqueous sodium bicarbonate solution and washed with water and brine. The organic phase was separated and concentrated to give approximately 10 g of crude material that was purified by silica gel chromatography using an eluant of hexane and ethyl acetate (95:5 v/v). A 7.4 g yield of the silylated product was obtained. m/z (ES) 373 (M+H)$^+$ and 395 (M+Na)$^+$

Step C: Preparation of (2S)-2-{[tert-butyl(dimethyl)silyl]oxy}-3-phenoxypropan-1-ol

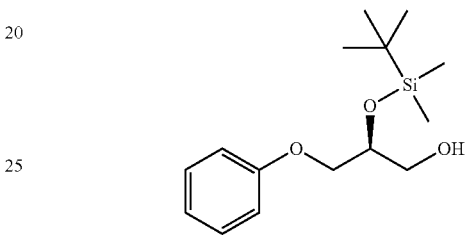

To the silyl-ether (7.2 g; 19.33 mmol) from Step B in ethanol (100 ml) as prepared was added 10% palladium on carbon (700 mg). The resulting reaction mixture was hydrogenated at room temperature at 40 psi for 16 hours on a Parr hydrogenator. The spent catalyst was removed by filtration and the filtrate thus obtained was concentrated under reduced pressure to afford the crude product. Purification of the crude product by silica gel chromatography using an eluant of hexanes and ethyl acetate (9:1 v/v) gave 4.85 g (89%) yield of the desired primary alcohol product. m/z (ES) 305 (M+Na)$^+$.

Step D: Preparation of (2R)-2-{[tert-butyl(dimethyl)silyl]oxy}-3-phenoxypropanal

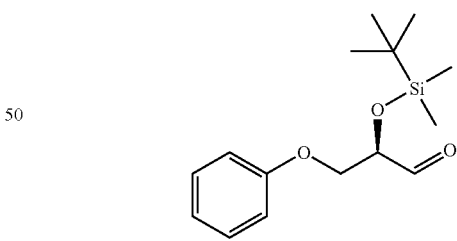

A solution of the primary alcohol (2.4 g; 8.5 mmol) from Step C above and Dess-Martin periodinate reagent (4.14 g; 9.77 mmol) in anhydrous methylene chloride (80 ml) was stirred at room temperature for 2 hours. The reaction was quenched with saturated aqueous sodium bicarbonate solution and then extracted with methylene chloride (3×60 ml). The combined methylene chloride extracts were dried over anhydrous sodium sulfate, filtered through a pad of silica gel and the filtrates thus obtained concentrated under reduced pressure to give 2.22 g (93%) of crude product that was judged to be of sufficient purity for use in Step E.

Step E: Preparation of (S)—N-((1E,2S)-2-{[tert-butyl(dimethyl)silyl]oxy}-3-phenoxypropylidene)-2-methylpropane-2-sulfinamide

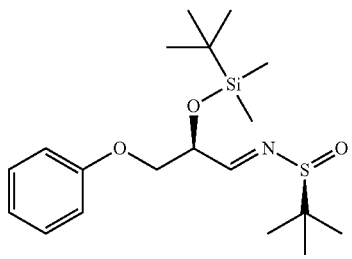 [SMILES: CC(C)(C)[S@](=O)/N=C/[C@@H](COc1ccccc1)O[Si](C)(C)C(C)(C)C]

Under a nitrogen inert atmosphere, a solution of the aldehyde (380 mg; 1.355 mmol) from Step D and (S)-(−)-2-methyl-2-propanesulfinamide (410 mg; 338 mmol) in methylene chloride (10 ml) was stirred at room temperature and to this solution anhydrous copper sulfate powder (450 mg; 2.82 mmol) was added. The reaction mixture was stirred at ambient temperature overnight. The reaction was quenched with water and the two layers separated. The methylene chloride phase was dried over sodium sulfate, filtered and then concentrated under reduced pressure to afford 458 mg of the crude reaction product that used in Step F described below. m/z (ES) 384.5 (M+H)$^+$.

Step F: Preparation of (S)—N-[(1S)-1-((1S)-1-{[tert-butyl(dimethyl)silyl]oxy}-2-phenoxyethyl)pent-4-en-1-yl]-2-methylpropane-2-sulfinamide and (S)—N-[(1R)-1-((1S)-1-{[tert-butyl(dimethyl)silyl]oxy}-2-phenoxyethyl)pent-4-en-1-yl]-2-methylpropane-2-sulfinamide

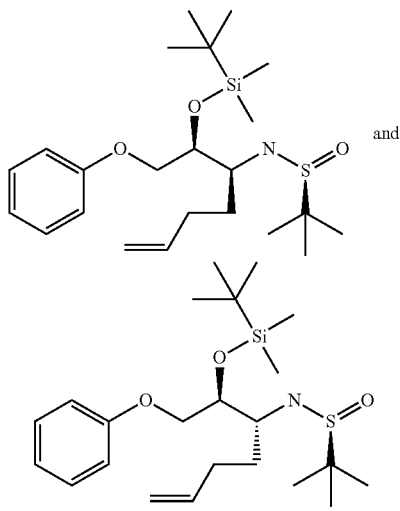

A solution of the sulfinamide (400 mg; 1.043 mmol) from Step E in anhydrous methylene chloride (10 ml) was stirred at room temperature and to this solution 3-butenylmagnesium bromide in TEM (0.5 M) (4.2 ml; 2.08 mmol) was added drop by drop. The resulting reaction mixture stirred at room temperature for 1.5 hours and then the reaction mixture was quenched with saturated aqueous ammonium chloride solution and extracted with methylene chloride (3×70 ml). The methylene chloride extracts were combined and washed with brine and then dried over anhydrous sodium sulfate powder, filtered and concentrated under reduced pressure. The crude product (approx. 350 mg) that was obtained on evaporation was purified by preparative TLC on silica gel plates (20 cm×20 cm×1500 microns) eluted with hexanes and ethyl acetate (2:1 v/v). Two product containing bands (R$_f$~0.55 and 0.4) were isolated from the plates. The band with R$_f$~0.4 afforded 175 mg of N-[(1R)-1-((1S)-1-{[tert-butyl(dimethyl)silyl]oxy}-2-phenoxyethyl)pent-4-en-1-yl]-2-methylpropane-2-sulfinamide. m/z (ES) 440.2 (M+H)$^+$ The band with R$_f$~0.55 yielded an impure product that was re-purified by preparative TLC on silica gel plate (20 cm×20 cm×1000 microns) eluted with hexanes, ethyl acetate, and methylene chloride (3:1:1) from which 31 mg of N-[(1S)-1-((1S)-1-{[tert-butyl(dimethyl)silyl]oxy}-2-phenoxyethyl)pent-4-en-1-yl]-2-methylpropane-2-sulfinamide was obtained along with 22 mg of an unidentified impurity. m/z (ES) 440.2 (M+H)$^+$.

Step G: Preparation of (S)-2-methylpropane-2-sulfinamide-tert-butyl(dimethyl){[(1S,2R,5E)-2-methyl-6-(4-nitrophenyl)-1-(phenoxymethyl)hex-5-en-1-yl]oxy}silane (1:1)

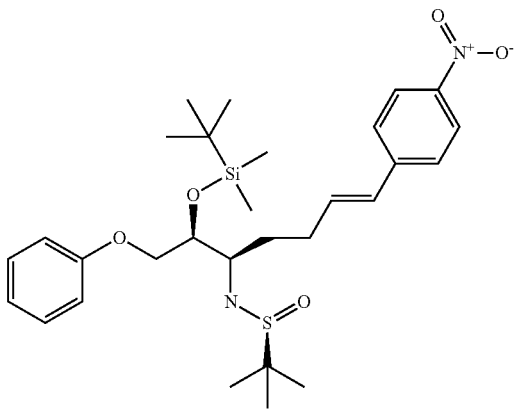 [SMILES: CC(C)(C)[S@](=O)N[C@H](CC/C=C/c1ccc([N+](=O)[O-])cc1)[C@@H](COc1ccccc1)O[Si](C)(C)C(C)(C)C]

The major product alkene, N-[(1R)-1-((1S)-1-{[tert-butyl(dimethyl)silyl]oxy}-2-phenoxyethyl)pent-4-en-1-yl]-2-methylpropane-2-sulfinamide (160 mg; 0.364 mmol) from Step F, 4-nitrostyrene (220 mg; 1.475 mmol) and Grubbs-II metathesis catalyst (45 mg; 0.053 mmol) were combined in anhydrous methylene chloride (6 ml) and the resulting reaction mixture stirred for 20 hours at 35° C. The crude product solution was concentrated under reduced pressure and the residues purified by silica gel plate chromatography on (20 cm×20 cm×1000 microns) eluted with hexanes and ethyl acetate (2:1 v/v) from which 116 mg of the desired metathesis product was obtained, m/z (ES) 561.22 (M+H)$^+$.

Step H: Preparation of (2S,3R,6E)-2-{[tert-butyl(dimethyl)silyl]oxy}-7-(4-nitrophenyl)-1-phenoxyhept-6-en-3-amine

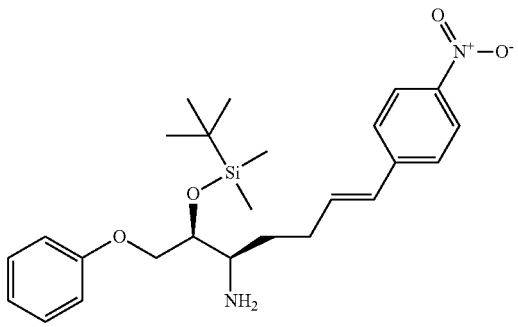 [SMILES: CC(C)(C)[Si](C)(C)O[C@H](COc1ccccc1)[C@H](N)CC/C=C/c1ccc([N+](=O)[O-])cc1]

The product (110 mg; 0.196 mmol) from Step G was dissolved in methylene chloride (3 ml) and to this resulting solution hydrogen chloride (4 M in dioxane) (0.3 ml) was added and the reaction mixture stirred for 0.25 hour. The volatiles were then removed by evaporation under reduced pressure to afford 95 mg of a crude product. The crude compound was used in Step I below without further purification. m/z (ES) 457.2 (M+H)+.

Step I: Preparation of (2R,5S)-2-((1S)-1-{[tert-butyl(dimethyl)silyl]oxy}-2-phenoxyethyl)-5-(4-nitrobenzyl)pyrrolidine and (2R,5R)-2-((1S)-1-{[tert-butyl(dimethyl)silyl]oxy}-2-phenoxyethyl)-5-(4-nitrobenzyl)pyrrolidine

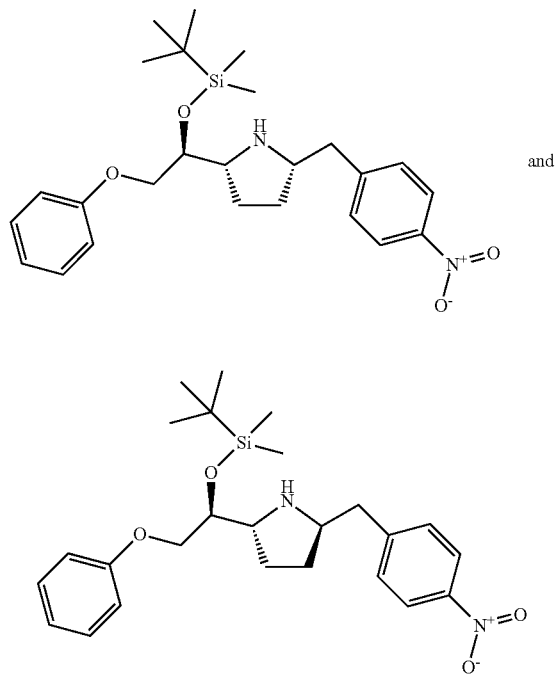 [SMILES: CC(C)(C)[Si](C)(C)O[C@H](COc1ccccc1)[C@H]1CC[C@@H](Cc2ccc([N+](=O)[O-])cc2)N1 ; CC(C)(C)[Si](C)(C)O[C@H](COc1ccccc1)[C@H]1CC[C@H](Cc2ccc([N+](=O)[O-])cc2)N1]

and

The crude primary amine was triturated in a small volume of dry methylene chloride and to this triethylamine (100 μL) was added and then the volatiles were removed under reduced pressure. The residues obtained from evaporation were dissolved in anhydrous DMF (10 ml) and to this solution diisopropylethylamine (150 μl) was added and the reaction mixture stirred for 3 hours at 70° C. to 80° C. then left to stir overnight at 40° C. and then cooled to room temperature. Ethyl acetate (10 ml) was added to the reaction mixture and this solution was washed with aqueous sodium bicarbonate solution (1 M) the layers separated and the aqueous layer back extracted with ethyl acetate (2×60 ml). The three ethyl acetate extracts were combined, washed with brine, dried over anhydrous sodium sulfate, filtered. The filtrate that was obtained was concentrated under reduced pressure to give a crude product. Purification of the crude material on preparative silica gel plates (20 cm×20 cm×1000 microns) eluted with hexanes, ethyl acetate and methylene chloride (1:1:1) afforded two products that had R$_f$ values of 0.55 and 0.4. m/z (ES) 457.2 (M+H)+.

The product that had an Rf~0.55 was (2R,5R)-2-((1S)-1-{[tert-butyl(dimethyl)silyl]oxy}-2-phenoxyethyl)-5-(4-nitrobenzyl)pyrrolidine, (17 mg) and the product with R$_f$~0.4 was (2R,5S)-2-((1S)-1-{[tert-butyl(dimethyl)silyl]oxy}-2-phenoxyethyl)-5-(4-nitrobenzyl)pyrrolidine (28 mg). m/z (ES) 457.2 (M±H)+.

Step J: Preparation of tert-butyl(2R,5S)-2-((1S)-1-{[tert-butyl(dimethyl)silyl]oxy}-2-phenoxyethyl)-5-(4-nitrobenzyl)pyrrolidine-1-carboxylate

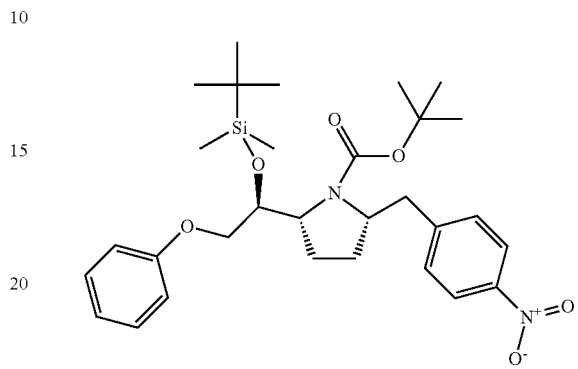

The major pyrrolidine product (2R,5S)-2-((1S)-1-{[tert-butyl(dimethyl)silyl]oxy}-2-phenoxyethyl)-5-(4-nitrobenzyl)pyrrolidine (16 mg; 0.035 mmol) from Step I and di-tert-butyl dicarbonate (15.3 mg; 0.07 mmol) were dissolved in methylene chloride (2 ml) and to the solution triethylamine (15 μl; 0.105 mmol) was added. The reaction mixture was stirred at room temperature for 20 hours and the reaction mixture concentrated under reduced pressure. Purification of the crude product using preparative silica gel plate (20 cm×20 cm×1000 microns) using an eluant of hexanes and ethyl acetate (85:15 v/v) and recovery of the product from the silica gel led to 17 mg (87%) of the desired BOC-protected pyrrolidine.

m/z (ES) 457.2 (M+H−Boc)+ and 579.2 (M+Na)+

Step K: Preparation of tert-butyl(2S,5R)-2-(4-aminobenzyl)-5-((1S)-1-{[tert-butyl(dimethyl)silyl]oxy}-2-phenoxyethyl)pyrrolidine-1-carboxylate

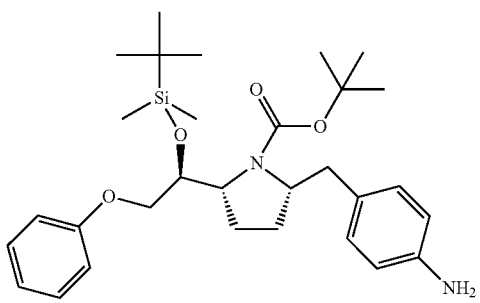 [SMILES: CC(C)(C)OC(=O)N1[C@H](Cc2ccc(N)cc2)CC[C@@H]1[C@@H](COc1ccccc1)O[Si](C)(C)C(C)(C)C]

A solution of the nitro compound (16 mg; 0.029 mmol) from Step J above in ethanol (2 ml) was prepared and to which 10%-palladium on carbon (15 mg) was suspended in solution. The mixture hydrogenated at atmospheric pressure and room temperature for 1.5 hours using a balloon reservoir of hydrogen gas. The spent catalyst was removed by filtration and the filtrate thus obtained was concentrated under reduced pressure to give 16 mg of crude material. Purification of the crude product by preparative TLC on silica gel plate (20 cm×20 cm×500 microns) using an eluant of hexanes and ethyl acetate (3:1 v/v) gave 9.3 mg (61%) of the desired aniline. m/z (ES) 427.3 (M+H-Boc)⁺

Step L: Preparation of tert-butyl(2S,5R)-2-{4-[({2-[(tert-butoxycarbonyl)amino]-1,3-thiazol-4-yl}acetyl)amino]benzyl}-5-((1S)-1-{[tert-butyl(dimethyl)silyl]oxy}-2-phenoxyethyl)pyrrolidine-1-carboxylate

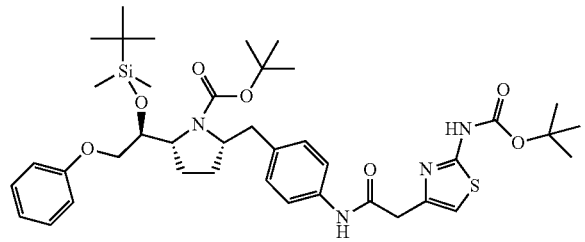 [SMILES: CC(C)(C)OC(=O)Nc1nc(CC(=O)Nc2ccc(C[C@@H]3CC[C@H]([C@@H](COc4ccccc4)O[Si](C)(C)C(C)(C)C)N3C(=O)OC(C)(C)C)cc2)cs1]

The aniline (9 mg; 0.017 mmol) from Step L and {2-[(tert-butoxycarbonyl)amino]-1,3-thiazol-4-yl}acetic acid (13.25 mg; 0.051 mmol) were dissolved in anhydrous methylene chloride (3 ml). To this solution EDC (9.8 mg; 0.051 mmol) and HOBt (5.25 mg; 0.034 mmol) and triethylamine (5 µL; 0.034 mmol) were added. The resulting reaction mixture was stirred for 18 hours at room temperature. The reaction was worked up by adding methylene chloride (3 ml) to the crude reaction and this diluted solution was washed with water (~5 ml) and the methylene chloride solution was dried over sodium sulfate and concentrated under reduced pressure. The crude product was purified by preparative silica gel plate (20 cm×20 cm×500 microns) eluted with hexanes and ethyl acetate (2:1 v/v). The desired amide product (9.2 mg; 70%) was obtained after purification. m/z (ES) 767.5 (M+H)⁺

Step M: Preparation of 2-(2-amino-1,3-thiazol-4-yl)-N-[4-({(2S,5R)-5-[(1S)-1-hydroxy-2-phenoxyethyl]pyrrolidine-2-yl}methyl)phenyl]acetamide bis trifluoroacetate salt

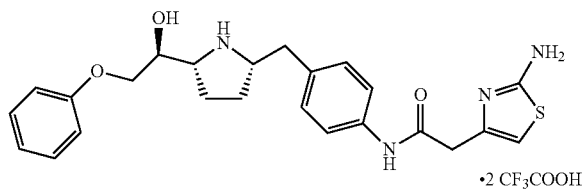 [SMILES: Nc1nc(CC(=O)Nc2ccc(C[C@@H]3CC[C@H]([C@H](O)COc4ccccc4)N3)cc2)cs1]

A solution of hydrogen chloride (4M in dioxane) (0.5 ml) was added to a solution of the amide (9 mg; 0.012 mmol) from Step L dissolved in methylene chloride (0.5 ml) and the resulting reaction solution was stirred at 50° C. for 2 hours. Hydrochloric acid (2M) (0.5 ml) was added and the reaction mixture was stirred vigorously overnight at room temperature. The crude reaction was evaporated to remove the volatiles under reduced pressure on a rotary evaporator and the residues from the evaporation were purified by mass directed reverse phase LC-MS (collecting m/z=453.5). After concentration of the product fractions obtained from the LC-MS purification, 5 mg (62.5%) of the bis trifluoroacetate salt of 2-(2-amino-1,3-thiazol-4-yl)-N-[4-({(2S,5R)-5-[(1S)-1-hydroxy-2-phenoxyethyl]pyrrolidine-2-yl}methyl)phenyl]acetamide was obtained. m/z (ES) 453.3 (M+H)⁺

Using the Functional Assay method described above, the human β3 functional activity (EC50) of Example 1 was determined to be <1 nM.

EXAMPLES 2-10

Examples 2-10 were prepared using procedures similar to those described in Example 1. Their human β3 functional activities (EC50) using the Functional Assay method described above are shown in Table 1, represented as the following ranges:
less than 1 nM (+); and
1-10 nM (++).

TABLE 1

| Example # | R | MS (ES) (M + H)⁺ | Human β3 EC₅₀ |
|---|---|---|---|
| 2 | benzotriazolylmethyl | 471.3 | ++ |
| 3 | (4-methylthiazol-2-yl)methyl | 452.3 | ++ |
| 4 | indazolylmethyl | 471.4 | ++ |
| 5 | (dimethylthiazolyl)methyl | 466.4 | ++ |
| 6 | (5-phenyl-4H-1,2,4-triazol-3-yl)methyl | 498.4 | + |
| 7 | (2-(2-pyrrol-1-ylethyl)-5-chlorophenyl)methyl | 544.3 | ++ |
| 8 | (4-methylphthalazin-1(2H)-on-2-yl)methyl | 513.5 | + |

TABLE 1-continued

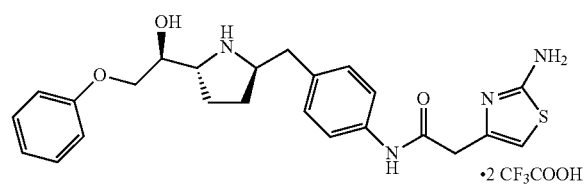

| Example # | R | MS (ES) (M + H)+ | Human β3 EC50 |
|---|---|---|---|
| 9 | (benzothiazol-2-yl-phenyl-methyl) | 550.4 | ++ |
| 10 | (2-oxoindolin-3-yl-methyl) | 516.4 | ++ |

EXAMPLE 11

2-(2-Amino-1,3-thiazol-4-yl)-N-[4-({(2R,5R)-5-[(1S)-1-hydroxy-2-phenoxyethyl]pyrrolidin-2-yl}methyl)phenyl]acetamide bis trifluoroacetate salt

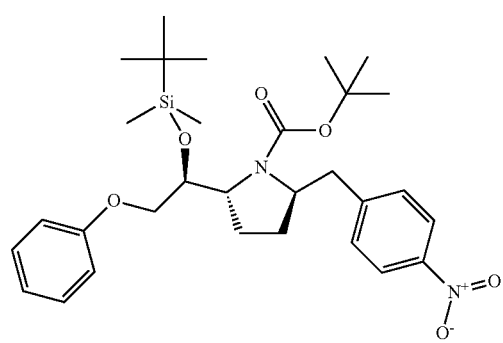 [SMILES: CC(C)(C)OC(=O)N1[C@@H](Cc2ccc([N+](=O)[O-])cc2)CC[C@@H]1[C@@H](COc1ccccc1)O[Si](C)(C)C(C)(C)C]

Step A: Preparation of tert-butyl(2R,5R)-2-(1S)-1-{[tert-butyl(dimethyl)silyl]oxy}-2-phenoxyethyl)-5-(4-nitrobenzyl)pyrrolidine-1-carboxylate The minor pyrrolidine product, (2R,5R)-2-((1S)-1-{[tert-butyl(dimethyl)silyl]oxy}-2-phenoxyethyl)-5-(4-nitrobenzyl)pyrrolidine (27 mg; 0.059 mmol) from Example 1 Step I above, di-tert-butyl dicarbonate (25.8 mg; 0.118 mmol) and triethylamine (15 µl; 0.105 mmol were dissolved in anhydrous methylene chloride (2 ml)) and allowed to react according to the method described in Example 1 Step J above for 20 hours. The crude reaction product was purified by preparative TLC on silica gel plate (20 cm×20 cm×500 microns) eluted with hexanes and ethyl acetate (85:15 v/v) to give the desired BOC-protected pyrrolidine title product (28 mg; 85%).

Step B: Preparation of tert-butyl(2R,5R)-2-(4-aminobenzyl)-5-((1S)-1-{[tert-butyl(dimethyl)silyl]oxy}-2-phenoxyethyl)pyrrolidine-1-carboxylate

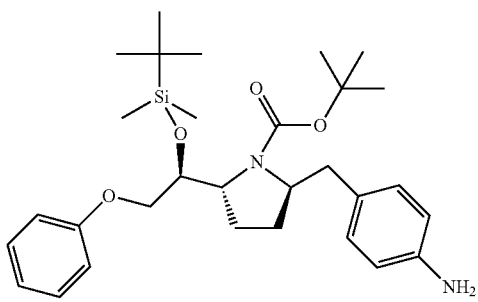 [SMILES: CC(C)(C)OC(=O)N1[C@@H](Cc2ccc(N)cc2)CC[C@@H]1[C@@H](COc1ccccc1)O[Si](C)(C)C(C)(C)C]

The BOC-protected pyrrolidine (27 mg; 0.048 mmol) was hydrogenated over 10% palladium on carbon (15 mg) in ethanol (2 ml) using the method described in Example 1 Step J. The crude product was purified by preparative TLC on a silica gel plate (20 cm×20 cm×500 microns) that was eluted with hexanes and ethyl acetate (3:1 v/v). The aniline (10.5 mg; 41%) product of the hydrogenation was isolated from the preparative TLC plate.

Step C: Preparation of tert-butyl(2R,5R)-2-{4-[({2-[(tert-butoxycarbonyl)amino]-1,3-thiazol-4-yl}acetyl)amino]benzyl}-5-((1S)-1-{[tert-butyl(dimethyl)silyl]oxy}-2-phenoxyethyl)pyrrolidine-1-carboxylate

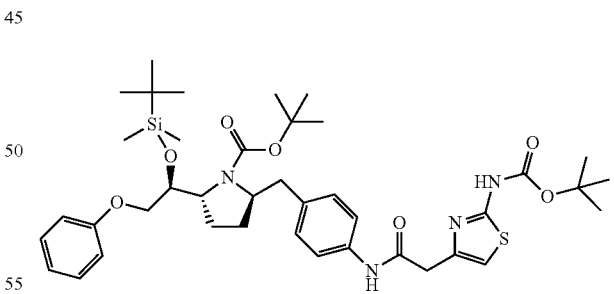

The aniline (9 mg; 0.017 mmol) from Step B above, {2-[(tert-butoxycarbonyl)amino]-1,3-thiazol-4-yl}acetic acid (13.25 mg; 0.051 mmol), EDC (9.8 mg; 0.051 mmol), HOBt (5.25 mg; 0.034 mmol) and triethylamine (5 µL; 0.034 mmol) in anhydrous methylene chloride (3 ml) were reacted together as described in Example 1 Step L for 18 hours at room temperature and worked up in a similar manner. After the workup the crude product was purified by preparative silica gel plate (20 cm×20 cm×500 microns) eluted with hexanes and ethyl acetate (2:1 v/v) from which the desired amide product (12 mg; 92%) was obtained.

Step D: Preparation of 2-(2-amino-1,3-thiazol-4-yl)-N-[4-({(2R,5R)-5-[(1S)-1-hydroxy-2-phenoxyethyl]pyrrolidin-2-yl}methyl)phenyl]acetamide bis trifluoroacetate salt

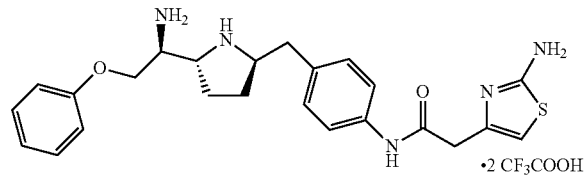 [SMILES: Nc1nc(CC(=O)Nc2ccc(C[C@H]3CC[C@H]([C@H](N)COc4ccccc4)N3)cc2)cs1]

A solution of hydrogen chloride (4M in dioxane) (0.5 ml) was added to a solution of the amide (12 mg; 0.012 mmol) from Step C above dissolved in methylene chloride (0.5 ml) and the resulting reaction solution was stirred at 50° C. for 2 hours. Hydrochloric acid (2M) (0.5 ml) was added and the reaction mixture was stirred vigorously overnight at room temperature and then worked up as follows. The crude reaction was evaporated to remove the volatiles under reduced pressure on a rotary evaporator and the residues from the evaporation were purified by mass directed reverse phase lc-ms (collecting m/z=453.5). After concentration of the product fractions obtained from the lc-ms purification, 9.1 mg (85%) of the bis trifluoroacetate salt of 2-(2-amino-1,3-thiazol-4-yl)-N-[4-({(2R,5R)-5-[(1S)-1-hydroxy-2-phenoxyethyl]pyrrolidine-2-yl}methyl)phenyl]acetamide was obtained. m/z (ES) 453.2 (M+H)+

Using the Functional Assay method described above, the human β3 functional activity (EC50) of Example 11 was determined to be 100-1000 nM.

EXAMPLE 12

N-[4-({(2S,5R)-5-[(1S)-1-Hydroxy-2-phenoxyethyl]pyrrolidin-2-yl}methyl)phenyl]-4-{4-[4-(trifluoromethyl)phenyl]-1,3-thiazol-2-yl}benzenesulfonamide trifluoroacetate salt

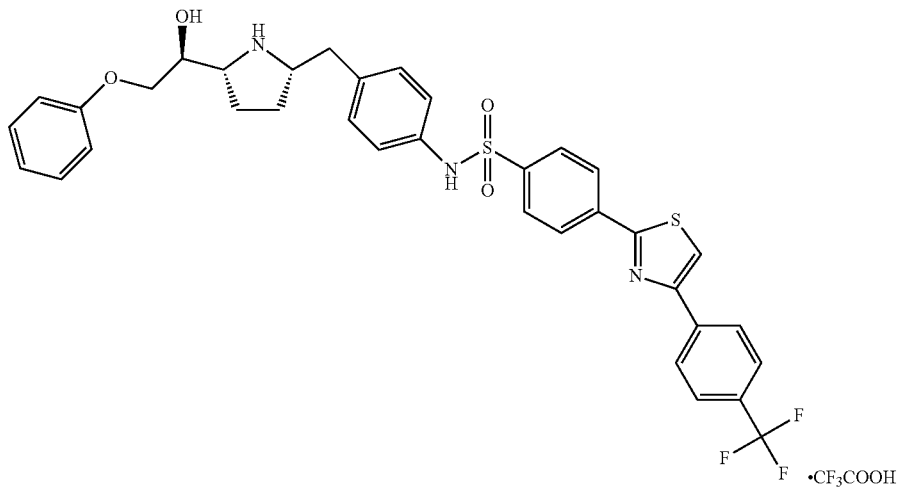 [SMILES: O=S(=O)(Nc1ccc(C[C@@H]2CC[C@H]([C@H](O)COc3ccccc3)N2)cc1)c1ccc(-c2nc(-c3ccc(C(F)(F)F)cc3)cs2)cc1 ; "·CF3COOH"]

Step A: tert-Butyl(2R,5S)-2-((1S)-1-{[tert-butyl(dimethyl)silyl]oxy}-2-phenoxyethyl)-5-(4-{[(4-{4-[4-(trifluoromethyl)phenyl]-1,3-thiazol-2-yl}phenyl)sulfonyl]amino}benzyl)pyrrolidine-1-carboxylate

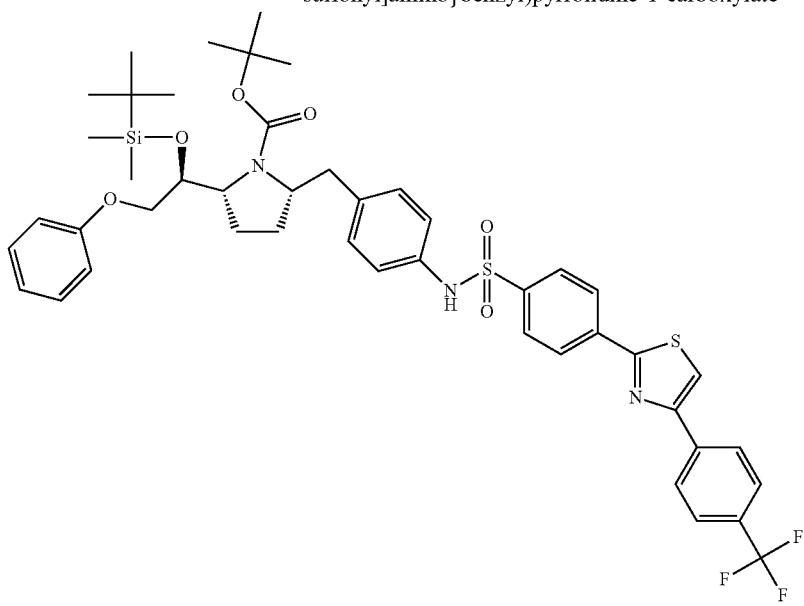

A solution of the aniline (23 mg; 0.044 mmol) from Example 1 Step K, 4-{4-[4-(trifluoromethyl)phenyl]-1,3-thiazol-2-yl}benzenesulfonyl chloride (44.1 mg; 0.109 mmol) (see R. J. Mathvink, et al., *J. Med. Chem.* 2000, 43, 3832-3836) and pyridine (1 ml) in anhydrous methylene chloride (3 ml) was stirred at 37° C. temperature overnight. The crude reaction product solution was concentrated under reduced pressure and the residues were dissolved in ethyl acetate and partitioned with water. The organic phase was separated, dried over anhydrous sodium sulfate powder and filtered then concentrated under reduced pressure. The crude product was purified by preparative tlc on a silica gel plate (20 cm×20 cm×500 microns) that were eluted with hexanes and ethyl acetate (2:1 v/v) to give 26 mg of the desired sulfonamide product. m/z (ES) 794.2 (M+H-Boc)+

Step B: N-[4-({(2S,5R)-5-[(1S)-1-Hydroxy-2-phenoxyethyl]pyrrolidin-2-yl}methyl)phenyl]-4-{4-[4-(trifluoromethyl)phenyl]-1,3-thiazol-2-yl}benzenesulfonamide trifluoroacetate salt

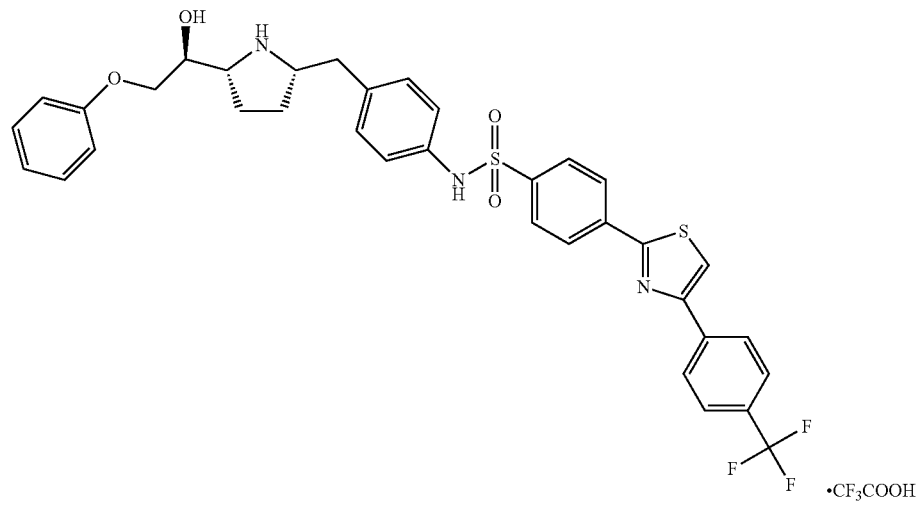 [SMILES: O=S(=O)(Nc1ccc(C[C@@H]2CC[C@H]([C@H](O)COc3ccccc3)N2)cc1)c1ccc(-c2nc(-c3ccc(C(F)(F)F)cc3)cs2)cc1 ; "·CF3COOH"]

A solution of the sulfonamide (20 mg; 0.022 mmol) described in Step A in anhydrous methylene chloride (2 ml) was treated with trifluoroacetic acid (1.5 ml) and the reaction mixture stirred for 4 hours at room temperature then at 40° C. for 3 hours. The crude reaction mixture was then concentrated under reduced pressure and the residues from the evaporation were purified by mass directed reverse phase lc-ms. The desired title sulfonamide (19 mg) was obtained as a TFA salt. m/z (ES) 680.2 (M+H)+

Using the Functional Assay method described above, the human β3 functional activity (EC50) of Example 12 was determined to be <10 nM.

EXAMPLE 13

Example 13 which has the following chemical structure was prepared using procedure similar to that described in Example 12. m/z (ES) 579.3 (M+H)+

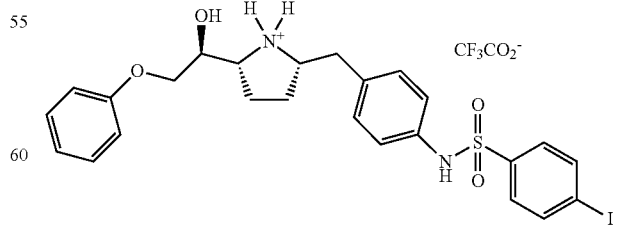

Using the Functional Assay method described above, the human β3 functional activity (EC50) of Example 13 was determined to be <10 nM.

EXAMPLE 14

4-{[(Hexylamino)carbonyl]amino}-N-[4-({(2S,5R)-5-[(1S)-1-hydroxy-2-phenoxyethyl]pyrrolidin-2-yl}methyl)phenyl]benzenesulfonamide trifluoroacetate salt

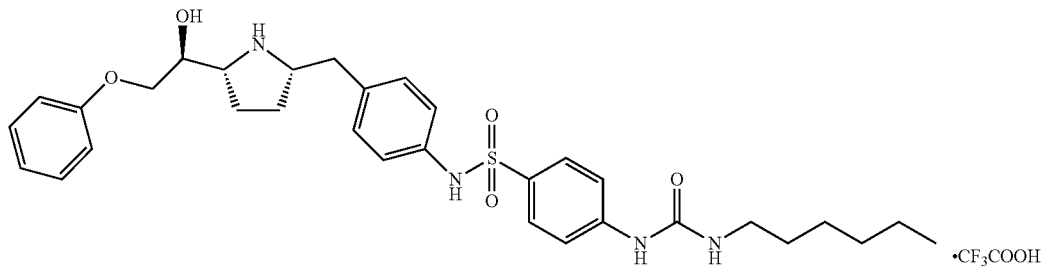 [SMILES: CCCCCCNC(=O)Nc1ccc(S(=O)(=O)Nc2ccc(C[C@@H]3CC[C@H]([C@H](O)COc4ccccc4)N3)cc2)cc1 ; "·CF3COOH"]

Step A: tert-4-{[(Hexylamino)carbonyl]amino}benzenesulfonyl chloride

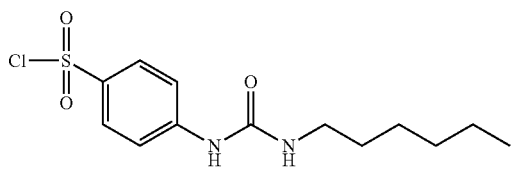 [SMILES: CCCCCCNC(=O)Nc1ccc(S(=O)(=O)Cl)cc1]

A solution of 4-(chlorosulfonyl)phenylisocyanate (50 mg; 0.23 mmol) in methylene chloride (4 ml) was cooled to −78° C. and to this solution n-hexylamine (30.2 mg; 0.299 mmol) was added. The solution was stirred for 0.5 hour and then allowed to warm to room temperature quickly; the volatiles were removed under reduced pressure on a rotary evaporator to give a crude product that was used in Step B below without further purification. m/z (ES) 319.2 (M+H)$^+$ Step B: tert-Butyl(2R,5S)-2-((1S)-1-{[tert-butyl(dimethyl)silyl]oxy}-2-phenoxyethyl)-5-(4-{[(4-{[(hexylamino)carbonyl]amino}phenyl)sulfonyl]amino}benzyl)pyrrolidine-1-carboxylate

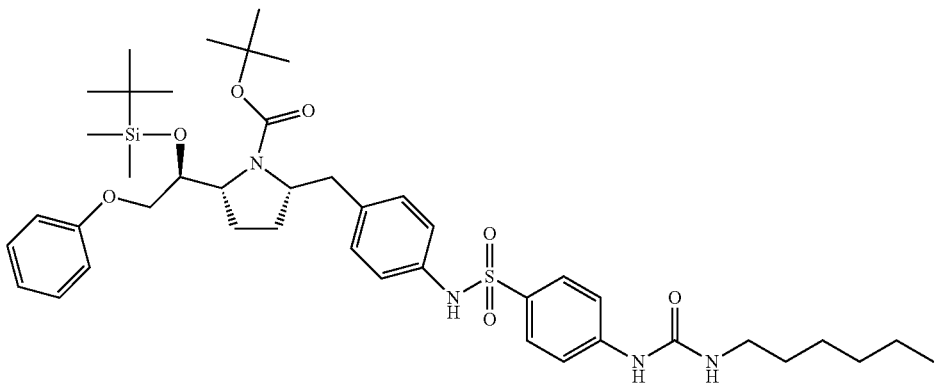 [SMILES: CCCCCCNC(=O)Nc1ccc(S(=O)(=O)Nc2ccc(C[C@@H]3CC[C@H]([C@@H](COc4ccccc4)O[Si](C)(C)C(C)(C)C)N3C(=O)OC(C)(C)C)cc2)cc1]

A solution of the aniline (20 mg; 0.038 mmol) from Example 1 Step K, benzenesulfonyl chloride (24.2 mg; 0.109 mmol) from Step A and pyridine (0.25 ml) in anhydrous methylene chloride (3 ml) was stirred at room temperature overnight. The crude reaction product solution was concentrated under reduced pressure and the residue was purified by preparative tlc on silica gel plate (20 cm×20 cm×500 microns) that were eluted with hexanes and ethyl acetate (1:1 v/v) to give 18 mg of the desired sulfonamide product. m/z (ES) 809.8 (M+H)$^+$ Step C: 4-{[(Hexylamino)carbonyl]amino}-N-[4-({(2S,5R)-5-[(1S)-1-hydroxy-2-phenoxyethyl]pyrrolidin-2-yl}methyl)phenyl]benzenesulfonamide trifluoroacetate salt

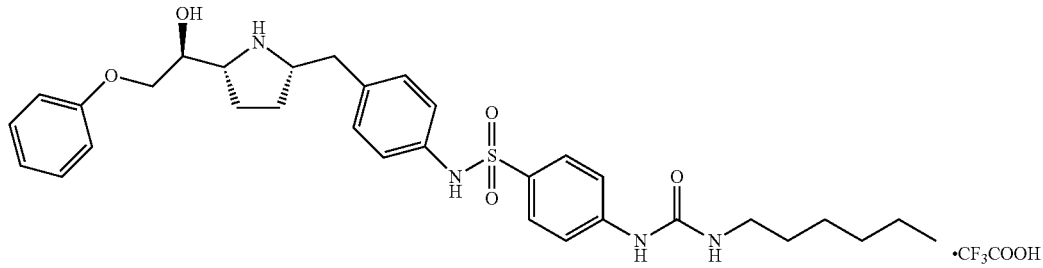 [SMILES: CCCCCCNC(=O)Nc1ccc(S(=O)(=O)Nc2ccc(C[C@@H]3CC[C@H]([C@H](O)COc4ccccc4)N3)cc2)cc1 ; "·CF3COOH"]

A solution of hydrogen chloride (4M in dioxane) (0.3 ml) was added to a solution of the amide (15 mg; 0.019 mmol) from Step B dissolved in methylene chloride (0.5 ml) and the resulting reaction solution was stirred at room temperature for 2 hours. The crude reaction mixture was evaporated under reduced pressure to remove the volatiles on a rotary evaporator and the residues from evaporation were purified by mass directed reverse phase lc-ms (collecting m/z=594.3). After concentration of the product fractions obtained from the lc-ms purification, 5 mg (62.5%) of the trifluoroacetate salt of 4-{[(hexylamino)carbonyl]amino}-N-[4-({(2S,5R)-5-[(1S)-1-hydroxy-2-phenoxyethyl]pyrrolidin-2-yl}methyl)phenyl]benzenesulfonamide trifluoroacetate salt was collected. m/z (ES) 595.6 (M+H)$^+$ Using the Functional Assay method described above, the human β3 functional activity (EC50) of Example 14 was determined to be <1 nM.

EXAMPLE 15

2-(3-Amino-1H-1,2,4-triazol-1-yl)-N-[4-({(2S,5R)-5-[(1S)-1-hydroxy-2-phenoxyethyl]pyrrolidin-2-yl}methyl)phenyl]acetamide trifluoroacetate salt

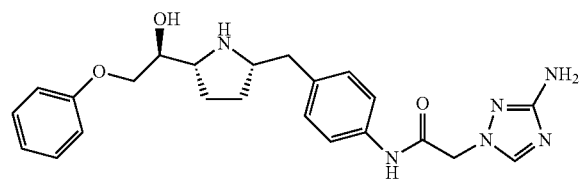 [SMILES: Nc1ncn(CC(=O)Nc2ccc(C[C@@H]3CC[C@H]([C@H](O)COc4ccccc4)N3)cc2)n1]

Step A: tert-Butyl(2R,5S)-2-((1S)-1-{[tert-butyl(dimethyl)silyl]oxy}-2-phenoxyethyl)-5-(4-{[(3-nitro-1H-1,2,4-triazol-1-yl)acetyl]amino}benzyl)pyrrolidine-1-carboxylate The title compound was prepared from the aniline (23 mg; 0.044 mmol) described in Example 1 Step K and (3-nitro-1H-1,2,4-triazol-1-yl)acetic acid (15.0 mg; 0.087 mmol) according to the procedure described in Example 1 Step L. After purification, 23 mg (77%) of the amide product was obtained. m/z (ES) 581.5 (M+H-Boc)$^+$ Step B: N-[4-({(2S,5R)-5-[(1S)-1-hydroxy-2-phenoxyethyl]pyrrolidin-2-yl}methyl)phenyl]-2-(3-nitro-1H-1,2,4-triazol-1-yl)acetamide trifluoroacetic acid salt

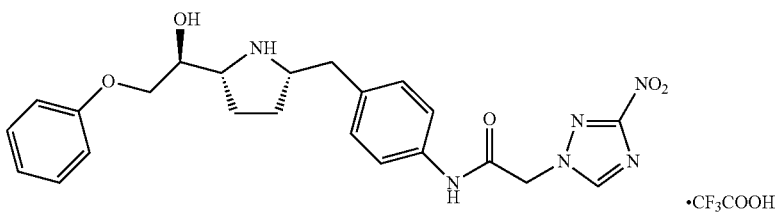 [SMILES: O=C(Cn1cnc([N+](=O)[O-])n1)Nc1ccc(C[C@@H]2CC[C@H]([C@H](O)COc3ccccc3)N2)cc1 ; "·CF3COOH"]

The amide (22 mg; 0.032 mmol) from Step A was dissolved in anhydrous methylene chloride (1.5 ml) and to this solution a 4 M hydrogen chloride solution in dioxane (1 ml) was added and the reaction mixture stirred at 80° C. for 20 minutes and then for 1 hour at 40° C. The volatiles were then removed under reduced pressure using a rotary evaporator and the residues that remained after evaporation were purified by mass directed reverse phase LC-MS. From the purification, 17 mg (91%) of the desired de-protected pyrrolidine as its trifluoroacetic acid salt was obtained. m/z (ES) 467.4 (M+H)$^+$ Step C: 2-(3-Amino-1H-1,2,4-triazol-1-yl)-N-[4-({(2S,5R)-5-[(1S)-1-hydroxy-2-phenoxyethyl]pyrrolidin-2-yl}methyl)phenyl]acetamide trifluoroacetate salt

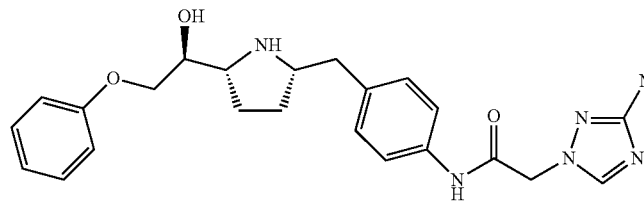

The salt product of Step B above was dissolved in a solvent mixture comprising ethanol (2 ml) and methanol (2 ml). The resulting solution was hydrogenated over 10% palladium on carbon (15 mg) at room temperature and atmospheric pressure. After 2 hours the hydrogenation reaction was complete as confirmed by analytical LC-MS. The reaction was worked up by filtering the reaction mixture and the filtrates thus obtained were concentrated under reduced pressure to afford 11 mg (89%) of the desired aminotriazole. m/z (ES) 437.4 (M+H)$^+$ Using the Functional Assay method described above, the human β3 functional activity (EC50) of Example 15 was determined to be <1 nM.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the active agents used in the instant invention as indicated above. Likewise, the specific pharmacological responses observed may vary according to and depending upon the particular active compound selected or whether there are present pharmaceutical carriers, as well as the type of formulation employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of Formula I, or a pharmaceutically acceptable salt thereof, or a stereoisomer thereof, or a pharmaceutically acceptable salt of the stereoisomer thereof:

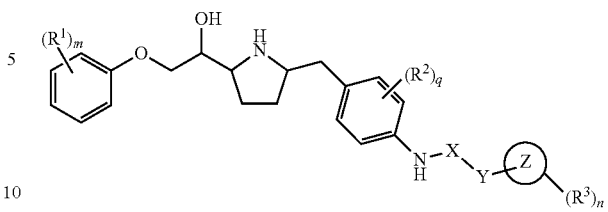

wherein
m is 0, 1, 2, 3, or 4;
n is 0, 1, 2, 3, 4, or 5;
p is 0, 1, or 2;
q is 0, 1, 2, 3, or 4;
X is —CO— or —SO$_2$—;
Y is selected from the group consisting of:
  (1) C$_1$-C$_3$ alkylene, optionally substituted with —NR$^2$R$^2$ or hydroxy,
  (2) —N(R$^6$)—,
  (3) —O—,
  (4) a bond, and
  (5) phenylene, optionally substituted with 1 to 3 groups independently selected from R$^1$;
Z is selected from the group consisting of:
  (4) a 5- or 6-membered heterocyclic ring with from 1 to 4 heteroatoms selected from oxygen, sulfur and nitrogen,
R$^1$ is selected from the group consisting of:
  (1) C$_1$-C$_{10}$ alkyl, optionally substituted with 1 to 5 groups selected from the group consisting of:
    (a) hydroxy,
    (b) halogen,
    (c) cyano,
    (d) QR$^2$,
    (e) C$_3$-C$_8$ cycloalkyl,
    (f) Q'COR$^3$,
    (g) —S(O)$_p$—NR$^2$R$^2$,
    (h) —N(R$^2$)SO$_2$R$^3$, and
    (i) Q'CO$_2$R$^2$,
  (2) C$_3$-C$_8$ cycloalkyl,
  (3) oxo,
  (4) halogen,
  (5) cyano,
  (6) QR$^2$,
  (7) —S(O)$_p$—NR$^2$R$^2$,
  (8) Q'COR$^3$,
  (9) —N(R$^2$)SO$_2$R$^3$,
  (10) Q'CO$_2$R$^2$, and
  (11) Z, optionally substituted with 1 to 5 groups selected from the group consisting of:
    (a) R$^2$,
    (b) QR$^2$,
    (e) halogen, and
    (d) oxo;

R² is selected from the group consisting of
 (1) hydrogen,
 (2) $C_1$-$C_{10}$ alkyl, optionally substituted with 1 to 5 groups selected from the group consisting of:
  (a) hydroxy,
  (b) halogen,
  (c) —$CO_2R^4$,
  (d) —$S(O)_p$—$C_1$-$C_{10}$ alkyl,
  (e) $C_3$-$C_8$ cycloalkyl,
  (f) $C_1$-$C_{10}$ alkoxy, optionally substituted with 1 to 5 halogens, and
  (g) Z, optionally substituted with 1 to 5 groups selected from the group consisting of halogen, trifluoromethyl, trifluoromethoxy, $C_1$-$C_{10}$ alkyl and $C_1$-$C_{10}$ alkoxy;
 (3) $C_3$-$C_8$ cycloalkyl,
 (4) Z, optionally substituted with 1 to 5 groups selected from the group consisting of:
  (a) halogen,
  (b) nitro,
  (c) oxo,
  (d) —$NR^4R^4$,
  (e) $C_1$-$C_{10}$ alkoxy, optionally substituted with 1 to 5 halogens,
  (f) —$S(O)_p$—$C_1$-$C_{10}$ alkyl, and
  (g) $C_1$-$C_{10}$ alkyl, optionally substituted with 1 to 5 groups selected from hydroxy, halogen, trifluoromethyl, cyano, —$CO_2R^4$, $C_3$-$C_8$ cycloalkyl, and $QR^5$;
R³ is selected from the group consisting of:
 (1) oxo,
 (2) halogen,
 (3) R², and
 (4) —$NR^2R^2$;
R⁴ is selected from the group consisting of:
 (1) hydrogen, and
 (2) $C_1$-$C_{10}$ alkyl;
R⁵ is selected from the group consisting of:
 (1) Z, optionally substituted with 1 to 5 groups selected from the group consisting of halogen, trifluoromethyl, cyano, $C_1$-$C_{10}$ alkyl, and $C_1$-$C_{10}$ alkoxy, and
 (2) $C_1$-$C_{10}$ alkyl;
R⁶ is selected from the group consisting of:
 (1) hydrogen, and
 (2) $C_1$-$C_{10}$ alkyl;
Q is selected from the group consisting of:
 (1) —N(R²)—,
 (2) —O—, and
 (3) —$S(O)_p$—; and
Q' is selected from the group consisting of:
 (1) —N(R²)—,
 (2) —O—, and
 (3) a bond.

2. The compound of claim 1, wherein m is 0 or 1; q is 0 or 1; and n is 0, 1 or 2.

3. The compound of claim 2, wherein Y is methylene, —CH(CH₃)— or a bond.

4. The compound of claim 2 wherein Z is selected from the group consisting of thiazolyl, oxazolyl, 1,2,4-triazolyl, 1,2,3-triazolyl, tetrazolyl, pyrrolidinyl, imidazolyl, pyrazolyl, 1,2,4-oxadiazolyl and 1,2,5-oxadiazolyl.

5. The compound of claim 2, wherein R³ is selected from the group consisting of:
 (1) $C_1$-$C_6$ alkyl optionally substituted with 1 to 3 halogens,
 (2) oxo,
 (3) halogen,
 (4) Z, optionally substituted with 1 to 3 groups selected from the group consisting of halogen, —$NH_2$, $C_1$-C6 alkyl, and trifluoromethyl, and
 (5) —$NH_2$.

6. The compound of claim 2, wherein m is 0; q is 0; and n is 0 or 1.

7. A compound of Formula Ia, or a pharmaceutically acceptable salt thereof, or a stereoisomer thereof, or a pharmaceutically acceptable salt of the stereoisomer thereof:

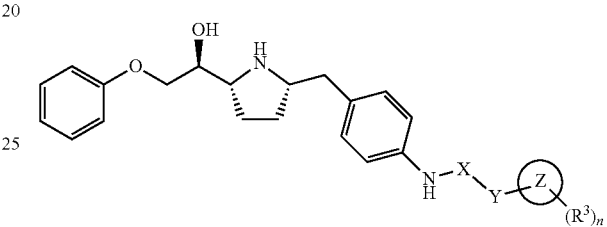

Ia wherein
n is 0, 1 or 2;
X is —CO— or —$SO_2$—;
Y is selected from the group consisting of methylene, —CH(CH₃)—, and a bond;
Z is selected from the group consisting of thiazolyl, 1,2,3-triazolyl, 1,2,4-triazolyl, and pyrazoly; and
R³ is selected from the group consisting of:
 (1) $C_1$-C6 alkyl, optionally substituted with 1 to 3 halogens,
 (2) oxo,
 (3) Z, optionally substituted with 1 to 3 groups selected from the group consisting of halogen, —$NH_2$, $C_1$-C6 alkyl, and trifluoromethyl, and
 (4) —$NR^2R^2$, wherein each occurrence of R² is independently hydrogen or $C_1$-C6 alkyl.

8. The compound of claim 7, wherein n is 0 or 1.

9. The compound of claim 7, wherein Y is methylene or a bond.

10. The compound of claim 7, wherein R³ is selected from the group consisting of:
 (1) methyl,
 (2) oxo,
 (3) —$NH_2$, and
 (4) —NH—$C_1$-C6 alkyl.

11. A compound of claim 1 selected from the group consisting of:

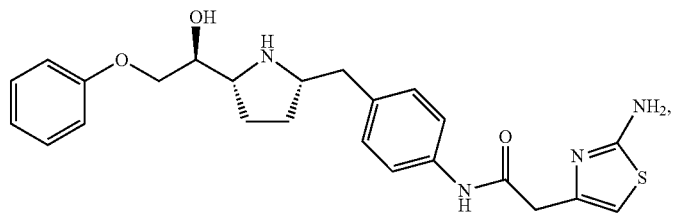 [SMILES: Nc1ncn(CC(=O)Nc2ccc(C[C@@H]3CC[C@H]([C@H](O)COc4ccccc4)N3)cc2)n1]

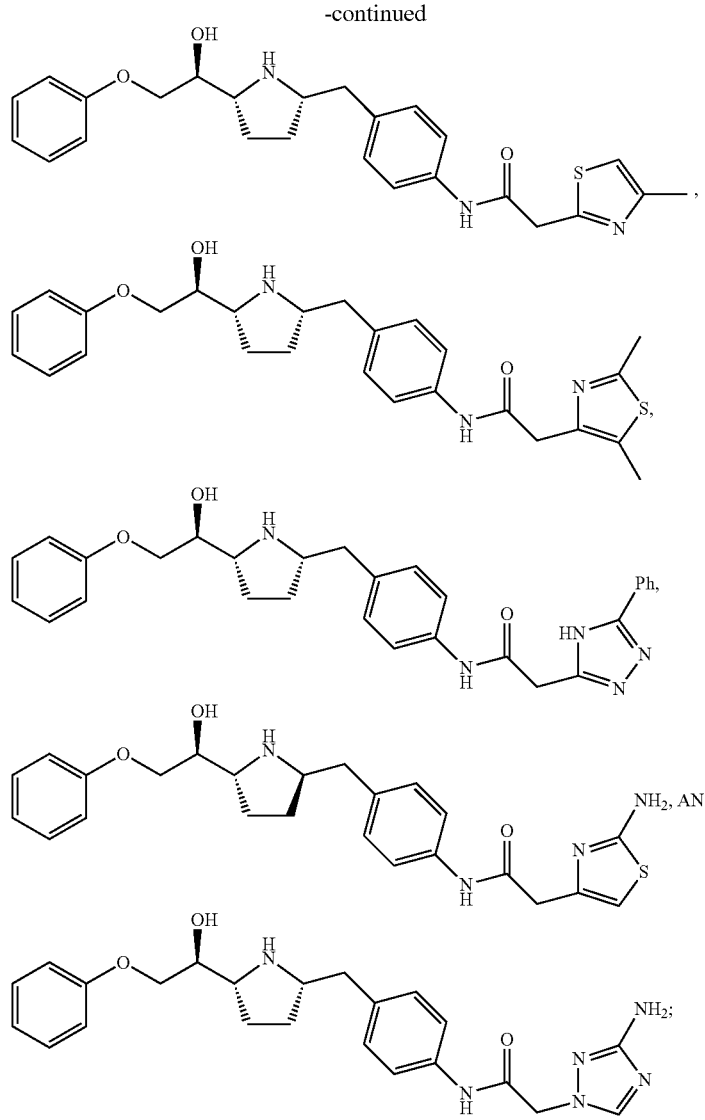

or a pharmaceutically acceptable salt thereof, or a pharmaceutically acceptable stereoisomer thereof, or a pharmaceutically acceptable salt of the stereoisomer thereof.

12. A pharmaceutical composition comprising a compound of claim 1 and a pharmaceutically acceptable carrier.

13. A method for the treatment or prevention of a disease or disorder mediated by the activation of β3-adrenoceptor, wherein said method comprises administering to a patient in need thereof a therapeutically effective amount of a compound of claim 1.

14. The method of claim 13 wherein the disease or disorder is selected from the group consisting of (1) overactive bladder, (2) urinary incontinence, (3) urge urinary incontinence, and (4) urinary urgency.

15. The method of claim 14, wherein the method comprises administering to a patient in need thereof a therapeutically effective amount of a compound of claim 1 and one or more other active ingredients.

* * * * *